(12) United States Patent
Plos et al.

(10) Patent No.: US 7,189,266 B2
(45) Date of Patent: Mar. 13, 2007

(54) DYEING COMPOSITION FOR HUMAN KERATINOUS FIBRES WITH DIRECT DYES AND DICATIONIC COMPOUNDS

(75) Inventors: Grégory Plos, Paris (FR); Henri Samain, Bievres (FR)

(73) Assignee: L'Oreal, S.A., Paris (FR)

( * ) Notice: Subject to any disclaimer, the term of this patent is extended or adjusted under 35 U.S.C. 154(b) by 371 days.

(21) Appl. No.: 10/480,168

(22) PCT Filed: Jun. 10, 2002

(86) PCT No.: PCT/FR02/01981

§ 371 (c)(1),
(2), (4) Date: Jul. 19, 2004

(87) PCT Pub. No.: WO02/100367

PCT Pub. Date: Dec. 19, 2002

(65) Prior Publication Data

US 2004/0237213 A1 Dec. 2, 2004

(30) Foreign Application Priority Data

Jun. 12, 2001 (FR) .................. 01 7682

(51) Int. Cl.
*A61K 7/13* (2006.01)
(52) U.S. Cl. ............... 8/405; 8/428; 8/437; 8/451; 8/455; 8/466; 8/552; 8/565; 8/566; 8/567; 8/570; 8/573; 548/302.4; 534/608; 544/180
(58) Field of Classification Search ............ 8/405, 8/428, 437, 451, 455, 466, 552, 565, 566, 8/567, 570, 573; 548/302.4; 534/608; 544/180
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,578,386 A | 5/1971 | Kalopissis et al. |
| 3,632,559 A | 1/1972 | Matter et al. |
| 3,836,537 A | 9/1974 | Boerwinkle et al. |
| 3,874,870 A | 4/1975 | Green et al. |
| 3,879,376 A | 4/1975 | Vanlerberghe et al. |
| 3,912,808 A | 10/1975 | Sokol |
| 3,915,921 A | 10/1975 | Schlatzer |
| 3,929,990 A | 12/1975 | Green et al. |
| 3,953,608 A | 4/1976 | Vanlerberghe et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |
| 4,025,945 A | 5/1977 | Bridgewater |
| 4,027,020 A | 5/1977 | Green et al. |
| 4,031,025 A | 6/1977 | Vanlerberghe et al. |
| 4,157,388 A | 6/1979 | Christiansen |
| 4,165,367 A | 8/1979 | Chakrabarti |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,240,450 A | 12/1980 | Grollier et al. |
| 4,277,581 A | 7/1981 | Vanlerberghe et al. |
| 4,349,532 A | 9/1982 | Vanlerberghe et al. |
| 4,381,919 A | 5/1983 | Jacquet et al. |
| 4,390,689 A | 6/1983 | Jacquet et al. |
| 4,422,853 A | 12/1983 | Jacquet et al. |
| 4,445,521 A | 5/1984 | Grollier et al. |

(Continued)

FOREIGN PATENT DOCUMENTS

DE        41 28 490 A1      3/1993

(Continued)

OTHER PUBLICATIONS

STIC Search Report (Aug. 8, 2006).*
M.R. Porter, "Handbook of Surfactants", Blackie & Son, Ltd., pp. 117-178, 1991.
G. Fonnum, J. Bakke & F.K. Hansen, "Associative Thickeners, Part I: Synthesis, Rheology and Aggregation Behavior", Colloid & Polymer Science, vol. 271, No. 4, Apr. 1993, The University of Trondheim, Laboratory of Organic Chemistry, Trtondheim, Norway, pp. 380-389.
International Search Report for PCT/FR 02/01781, dated Oct. 11, 2002, Authorized Officer: D. Voyiazoglou.
English language Derwent for FR 2 077 143.
English language Derwent for FR 2 080 759.
English language Derwent for FR 2 320 330.
English language Derwent for FR 2 336 434.
English language Derwent for EP 080 976.
English language Derwent for DE 41 28 490 A1.
English language Derwent for DE 198 02 940 C2.
English language Derwent for EP 1 133 975 A2.

*Primary Examiner*—Eisa Elhilo
(74) *Attorney, Agent, or Firm*—Finnegan, Henderson, Farabow, Garrett, & Dunner, L.L.P.

(57) ABSTRACT

The present disclosure relates to a composition for dyeing human keratin fibers, such as the hair, comprising, in a medium suitable for dyeing, at least one direct dye and at least on dicationic compound. Also disclosed herein is a process for dyeing and lightening human keratin fibers, such as the hair, with the compositions disclosed, as well as a the corresponding dyeing kits.

31 Claims, No Drawings

U.S. PATENT DOCUMENTS

| | | | |
|---|---|---|---|
| 4,509,949 A | 4/1985 | Huang et al. | |
| 4,591,610 A | 5/1986 | Grollier | |
| 4,702,906 A | 10/1987 | Jacquet et al. | |
| 4,719,099 A | 1/1988 | Grollier et al. | |
| 4,719,282 A | 1/1988 | Nadolsky et al. | |
| 4,761,273 A | 8/1988 | Grollier et al. | |
| 4,823,985 A | 4/1989 | Grollier et al. | |
| 4,839,166 A | 6/1989 | Grollier et al. | |
| 4,948,579 A | 8/1990 | Jacquet et al. | |
| 4,996,059 A | 2/1991 | Grollier et al. | |
| 5,009,880 A | 4/1991 | Grollier et al. | |
| 5,089,252 A | 2/1992 | Grollier et al. | |
| 5,125,930 A | 6/1992 | Taniguchi | |
| 5,139,037 A | 8/1992 | Grollier et al. | |
| 5,196,189 A | 3/1993 | Jacquet et al. | |
| 5,674,299 A | 10/1997 | Käser et al. | |
| 5,708,151 A * | 1/1998 | Mockli | 534/608 |
| 5,958,392 A | 9/1999 | Grollier et al. | |
| 6,458,167 B1 | 10/2002 | Genet et al. | |
| 2002/0004956 A1 | 1/2002 | Rondeau | |

FOREIGN PATENT DOCUMENTS

| | | |
|---|---|---|
| DE | 198 02 940 C2 | 8/1999 |
| EP | 080 976 | 6/1983 |
| EP | 0 122 324 | 10/1984 |
| EP | 0 216 479 B2 | 4/1987 |
| EP | 0 318 294 B1 | 5/1989 |
| EP | 0 337 354 B1 | 10/1989 |
| EP | 0 696 619 B1 | 2/1996 |
| EP | 0 714 954 B1 | 6/1996 |
| EP | 1 022 016 A2 | 7/2000 |
| EP | 1 133 975 A2 | 9/2001 |
| FR | 1 400 366 | 5/1965 |
| FR | 1 583 363 | 10/1969 |
| FR | 2 077 143 | 10/1971 |
| FR | 2 080 759 | 11/1971 |
| FR | 2 137 684 | 12/1972 |
| FR | 2 190 406 | 2/1974 |
| FR | 2 252 840 | 6/1975 |
| FR | 2 270 846 | 12/1975 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 586 913 A1 | 3/1987 |
| FR | 2 598 611 | 11/1987 |
| GB | 1021400 | 3/1966 |
| WO | WO 95/01772 | 1/1995 |
| WO | WO 95/15144 | 6/1995 |
| WO | WO 98/44012 | 10/1998 |
| WO | WO 99/20235 | 4/1999 |
| WO | WO 02/31056 | 4/2002 |

* cited by examiner

DYEING COMPOSITION FOR HUMAN KERATINOUS FIBRES WITH DIRECT DYES AND DICATIONIC COMPOUNDS

The present invention relates to a dye composition for human keratin fibers, and more particularly the hair, comprising at least one direct dye and also at least one dicationic compound in a medium that is suitable for dyeing.

It is known practice to dye human keratin fibers, and in particular the hair, with dye compositions containing direct dyes, in particular nitrobenzene dyes, acidic azo dyes, cationic azo dyes, anthraquinone dyes and natural dyes.

These colorations may be performed by applying the composition containing the direct dye(s) directly onto the keratin fibers, or by applying a mixture, prepared extemporaneously, of a composition containing the direct dye(s) with a composition containing an oxidizing bleaching agent, which is preferably aqueous hydrogen peroxide solution. In this case, this process is termed lightening direct dyeing.

However, when they are incorporated into dye compositions, direct dyes have the drawback of leading to colorations that show insufficient fastness, in particular with respect to shampooing.

Certain di- or tricationic dyes have already been described and proposed for coloring paper; cationic diazomethines or triazomethines have thus been described in European patent no. 318 294 B1, and cationic azo- or diazoimidazoles have also been described in U.S. Pat. Nos. 5,708,151 and 5,674,299.

Moreover, European patent application no. 1 133 975 A2 discloses a hair dye composition especially comprising a direct dye having the following structure:

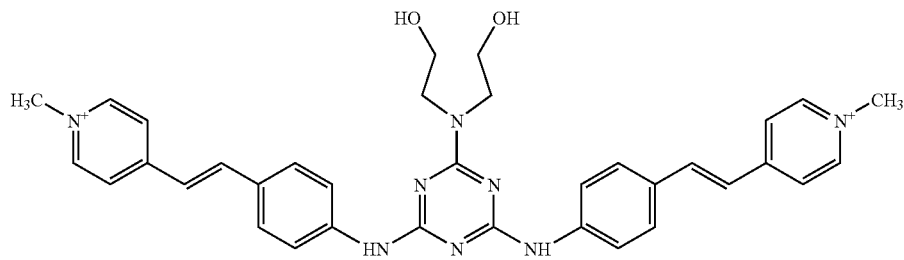

The Applicant has now discovered that it is possible to obtain novel dyes capable of producing strong colorations, which show little selectivity and good resistance to the various attacking factors to which the hair may be subjected, by combining a conventional direct dye with at least one suitably selected dicationic compound.

This discovery forms the basis of the present invention.

Now, after considerable research conducted in this matter, the Applicant has discovered that it is possible to obtain dye compositions with known direct dyes, which make it possible to obtain shades that show good resistance to the various attacking factors to which the hair may be subjected (light, bad weather, washing, permanent-waving, perspiration and rubbing) and in particular to shampooing, if dicationic compounds chosen from those of formulae (I), (II) (III) and (IV) described below are introduced into said dye compositions.

The shades obtained with said combinations of dyes are moreover strong, chromatic (luminous) and show little selectivity, i.e. they produce small differences in coloration along the same length of keratin fiber, which may in fact be differently sensitized (i.e. damaged) between its end and its root.

These discoveries form the basis of the present invention.

A first subject of the present invention is thus a composition for dyeing human keratin fibers, and more particularly the hair, comprising at least one direct dye in a medium that is suitable for dyeing, characterized in that it also comprises at least one dicationic compound chosen from those of formula (I), (II) or (III) described below, and a dye composition for human keratin fibers, and more particularly the hair, comprising, in a medium that is suitable for dyeing, at least one dicationic compound of formula (IV) defined below and at least one direct dye different than the group formed by the basic dyes generally referred to in the field of coloration as "BASIC DYES", including Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1), Basic Yellow 57 (C.I. 12719).

Another subject of the invention relates to a ready-to-use composition for dyeing human keratin fibers, and in particular the hair, which contains at least one direct dye, at least one dicationic compound of formula (I), (II), (III) or (IV), and an oxidizing agent.

For the purposes of the invention, the term "ready-to-use composition" means the composition intended to be applied in unmodified form to the keratin fibers, i.e. it may be stored in unmodified form before use or may result from the extemporaneous mixing of two or more compositions.

The invention is also directed toward a process for the direct dyeing of human keratin fibers, and in particular the hair, which consists in applying to the fibers a composition containing, in a medium that is suitable for dyeing, at least one direct dye and at least one dicationic compound of formula (I), (II), (III) or (IV).

The invention is also directed toward a process for the lightening direct dyeing of human keratin fibers, and in particular the hair, which consists in applying to the fibers an extemporaneous mixture of a composition containing, in a medium that is suitable for dyeing, at least one direct dye and at least one dicationic compound of formulae (I), (II), (III) and (IV) and a composition containing at least one oxidizing agent.

A subject of the invention is also a device for the lightening direct dyeing of human keratin fibers, and in particular the hair, or a dyeing "kit", which comprises a first compartment containing, in a medium that is suitable for dyeing, at least one direct dye and at least one dicationic compound of formula (I), (II), (III) or (IV), and a second compartment containing an oxidizing agent.

This device may be equipped with a means for applying the desired mixture to the hair, such as the devices described in patent FR-2 586 913 in the name of the Applicant.

However, other characteristics, aspects, subjects and advantages of the invention will emerge even more clearly on reading the description and the examples that follow.

Dicationic Direct Dye

The dicationic direct dyes according to the present invention are chosen from those of formula (I), (II), (III) or (IV) below:

$$[A-\underset{R_1}{N}-Z-\underset{R_2}{N}]_2-X \quad (I)$$

$$A-\underset{R_1}{N}-Z_1-\underset{R_2}{N}-A_1 \quad (II)$$

in which formula (I) or (II):

A and A1, independently of each other, denote a radical of formula (a) below (a)

[structure with $R_3$, $R_5$, $R_6$, $R_4$, An⁻, N=N]

Z denotes an aliphatic or aromatic radical, $Z_1$ denotes an alkyl radical, $R_1$ and $R_2$, independently of each other, denote a hydrogen atom or a ($C_1$–$C_4$)alkyl radical, or a ($C_1$–$C_4$)alkyl radical substituted with one or more halogen atoms, a hydroxyl, carboxyl or cyano radical, a ($C_1$–$C_4$)alkoxy radical, a ($C_1$–$C_4$)alkoxy radical substituted with one or more hydroxyl or ($C_1$–$C_4$)alkoxy radicals, or an amino, alkylamino, dialkylamino, aminocarbonyl, phenyl, phenoxy or phenylaminocarbonyl radical, in which the phenyl radical is unsubstituted or substituted with a ($C_1$–$C_4$)alkyl, ($C_1$–$C_4$)alkoxy or phenoxy radical, or $R_1$ and $R_2$ form, together with the two nitrogen atoms that bear them and the radical Z, a piperazine ring, X is a bridging radical chosen from: —CO—; —CO—$CH_2$—$CH_2$—CO—; —CO—CO—; 1,4-dicarbonylphenyl; —$CH_2$—$CH_2$—; or a triazine of formula (b) or (c) below:

(b)

[triazine structure with Y]

or

-continued (c)

[bis-triazine structure with Y, $Y_1$, $Z_2$, $R_1$, $R_2$]

in which:

Y and Y1, independently of each other, denote a halogen atom or a hydroxyl, amino, monoalkylamino, dialkylamino, 1-piperidino, morpholino or 1-piperazino radical, the piperazino radical being unsubstituted or substituted on the nitrogen atom not attached to the triazine ring with a ($C_1$–$C_4$)alkyl radical, said alkyl radicals being unsubstituted or substituted with hydroxyl, amino, mono($C_1$–$C_4$)alkylamino or di($C_1$–$C_4$) alkylamino, $Z_2$ denotes a ($C_2$–$C_8$)alkylene radical or forms a piperazine ring with the two adjacent nitrogen atoms and the radicals $R_1$ and $R_2$, in the radical of formula (a), $R_3$ and $R_4$, independently of each other, denote a hydrogen atom or a ($C_1$–$C_4$)alkyl radical, or ($C_1$–$C_4$)alkyl substituted with one or more halogen atoms, a hydroxyl, carboxyl, or cyano radical, a ($C_1$–$C_4$)alkoxy radical, a ($C_1$–$C_4$)alkoxy radical substituted with a hydroxyl or ($C_1$–$C_4$)alkoxy radical, or an amino, alkylamino, dialkylamino, aminocarbonyl, phenyl, phenoxy or phenylaminocarbonyl radical, in which the phenyl radical is unsubstituted or substituted with a ($C_1$–$C_4$)alkyl, ($C_1$–$C_4$)alkoxy or phenoxy radical, $R_5$ and $R_6$, independently of each other, denote a hydrogen atom, a ($C_1$–$C_4$)alkyl or ($C_1$–$C_4$)alkoxy radical optionally substituted with a hydroxyl, carboxyl, halogen or cyano radical, a ($C_1$–$C_4$)alkoxy radical optionally substituted with a hydroxyl or ($C_1$–$C_4$)alkoxy radical, or an amino, alkylamino, dialkylamino, aminocarbonyl, phenyl, phenoxy or phenylaminocarbonyl radical, in which the phenyl radical is unsubstituted or substituted with a ($C_1$–$C_4$)alkyl, ($C_1$–$C_4$)alkoxy or phenoxy radical, An⁻ denotes an anion.

Preferably, according to the invention, in formula (I), $R_1$ and $R_2$, independently of each other, denote hydrogen, ($C_1$–$C_4$)alkyl substituted with hydroxyl or ($C_1$–$C_4$) alkoxy, and even more particularly denote hydrogen or methyl, Z denotes a linear, branched or cyclic $C_2$–$C_8$ alkyl radical optionally substituted with a hydroxyl, alkoxy or halogen, the chain of said radical optionally being interrupted with a group —O— or —$NR_1$—; a 1,4-phenyl radical, a 1,4-naphthyl radical optionally substituted with an alkyl, alkoxy or halogen; Z possibly forming a piperazine ring with $R_1$, $R_2$ and the 2 nitrogen atoms, Z preferably denotes an unsubstituted phenyl radical, a phenyl or naphthyl radical substituted with 1 or 2 methyl or methoxy radicals, a piperazine radical by bonding with $R_1$, $R_2$ and the 2 nitrogen atoms, or a ($C_2$–$C_4$)alkylene radical which is unsubstituted or substituted with one or two hydroxyls, X denotes a group of formula (b).

Preferably, according to the invention, in formula (II),
$Z_1$ denotes a linear, branched or cyclic $C_2$–$C_8$ alkyl radical, optionally substituted with a hydroxyl, alkoxy or halogen, the chain of said radical optionally being interrupted with a group —O— or —$NR_1$—; a piperazine ring formed with $R_1$, $R_2$ and the two nitrogen atoms, $Z_1$ preferably denotes a ($C_2$–$C_6$)alkylene radical which is unsubstituted or substituted with one or more hydroxyl, a piperazine ring formed with $R_1$, $R_2$ and the two nitrogen atoms; and even more particularly an unsubstituted ($C_2$–$C_4$)alkylene radical, $R_3$ and $R_4$ denote methyl or ethyl, and $R_5$ and $R_6$ denote hydrogen, methyl or methoxy.

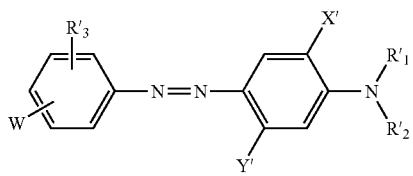
(III)

in which formula (III),
the number of cationic charges is two,
X' and Y', independently of each other, denote hydrogen, halogen, ($C_1$–$C_4$)alkyl, ($C_1$–$C_4$)alkoxy, ($C_1$–$C_4$)-alkylcarbonylamino, arylcarbonylamino, ureido or arylureido, $R'_1$ denotes hydrogen, a substituted alkyl or aryl radical, an unsubstituted alkyl or aryl radical, or the same meaning as $R'_2$ $R'_2$ is a radical of formula (d) below:

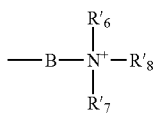
(d)

in which:
B denotes a linear or branched alkylene radical,
$R'_6$ denotes hydrogen or substituted or unsubstituted alkyl,
$R'_7$ and $R'_8$, independently of each other, denote substituted or unsubstituted alkyl,
$R'_6$ and $R'_7$, together with the nitrogen, form a substituted or unsubstituted 5-, 6- or 7-membered ring, which may contain other hetero atoms, or alternatively $R'_6$, $R'_7$ and $R'_8$ together form a pyridinium ring,
$R'_3$ denotes hydrogen, halogen, ($C_1$–$C_4$)alkyl or ($C_1$–$C_4$)-alkoxy,
W is a radical of formula (e) below:

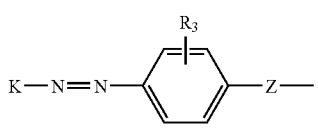
(e)

in which:
K is a coupling radical,

Z denotes a bridging radical chosen from the radicals of formulae:

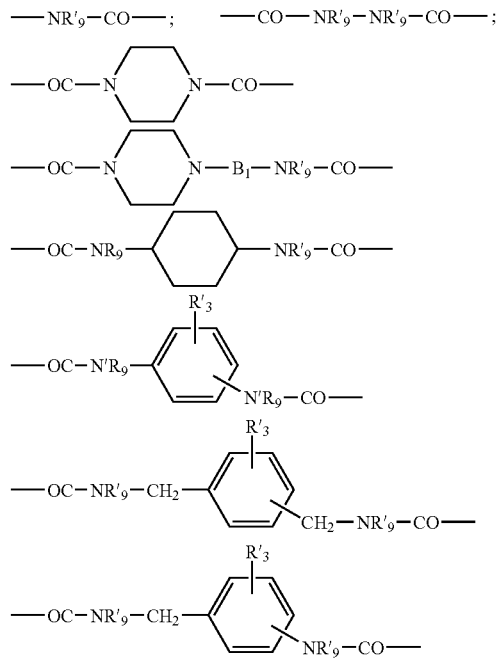

or —CO—$NR'_9$—$B_1$—$NR'_9$—CO—,
and in which $R'_9$ denotes hydrogen or unsubstituted or substituted ($C_2$–$C_4$)alkylene, the alkylene radical being linear or branched and possibly being interrupted with one or more groups chosen from: —NR'9—, —O— and —S—.

Preferably, according to the invention, in formula (III),
B denotes ethylene, n-propylene, isopropylene or n-butylene,
K denotes a coupling compound chosen from those of formula (f), (g) or (h) below

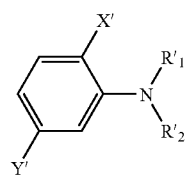
(f)

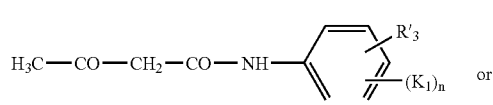
(g)

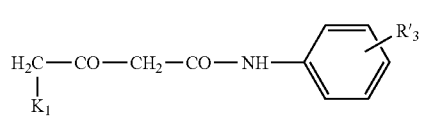
(h)

in which,
X', Y' and $R'_1$ and $R'_2$ have the same meaning as in formula (III),
n is equal to 1 or 2,
$K_1$ denotes the radical of formula:

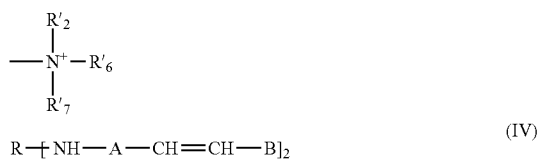

(IV)

in which formula (IV) the groups of formula —NH-A-CH=CH—B are identical or different and in which, A denotes a substituted or unsubstituted benzene ring, B denotes a radical derived from a heterocyclic compound containing quaternized nitrogen comprising an active methyl or methylene radical, R denotes the residue of a crosslinking agent chosen from phosgene, halogenated triazines and halogenated pyrimidines.

More particularly, each group B may denote a quinolinium, picolinium, benzothiazolium, benzimidazolium, indolium or quinoxalinium derivative; each group A may denote a benzene ring that is unsubstituted or substituted with one or more radicals chosen from $(C_1–C_4)$alkoxy, $(C_1–C_4)$alkyl or halogen; and R denotes a halogenated triazine chosen from 2,4,6-trichlorotriazine, 2,4,6-trifluorotriazine, 2,4-dichloro-6-(dimethylaminopropylamino)triazine, 2,4-dichloro-6-hydroxytriazine, 2,4-difluoro-6-(trimethylaminoethylamino)triazine chloride, 2,4-difluoro-6-(N-carboxymethylamino)triazine, 2,4-dichloro-6-(N,N-dihydroxyethylamino)triazine, 2,4-difluoro-6-(N-hydroxypropylamino)triazine, 2,4-dichloro-6-(N,N-dimethylamino)triazine, 2,4-difluoro-6-(N,N-dihexylamino-triazine and 2,4-dichloro-6-(N-2-sulfoethylamino)triazine.

According to the present invention, among the compounds of formula (I) that may be mentioned more particularly is the compound sold by the company CIBA under the name Pergasol Violet F-R, having the following formula:

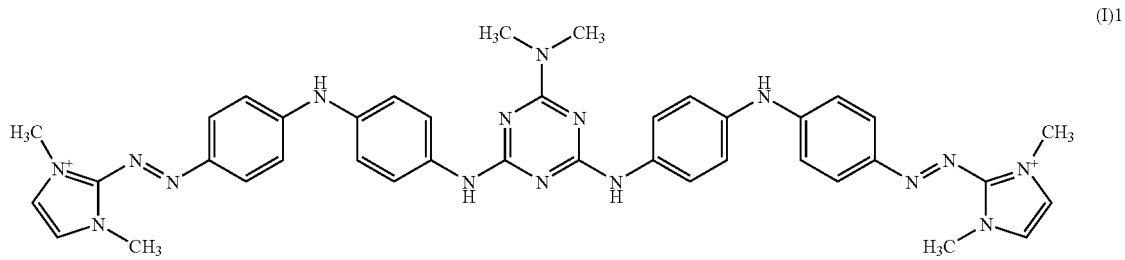

(I)1

Mention may also be made of the compounds of formula (I) corresponding to formulae (I)2 to (I)7 below:

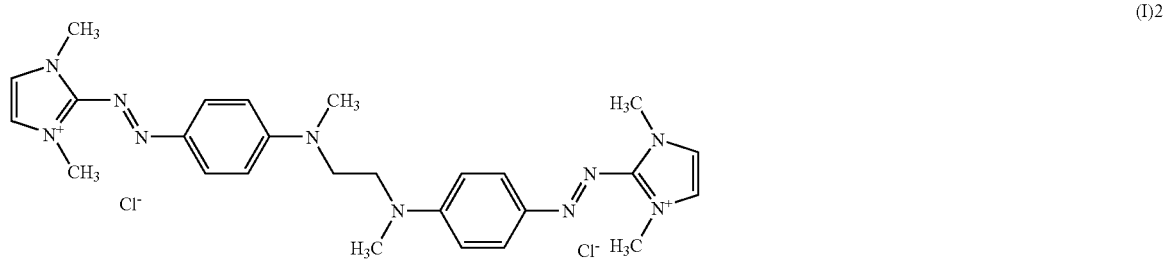

(I)2

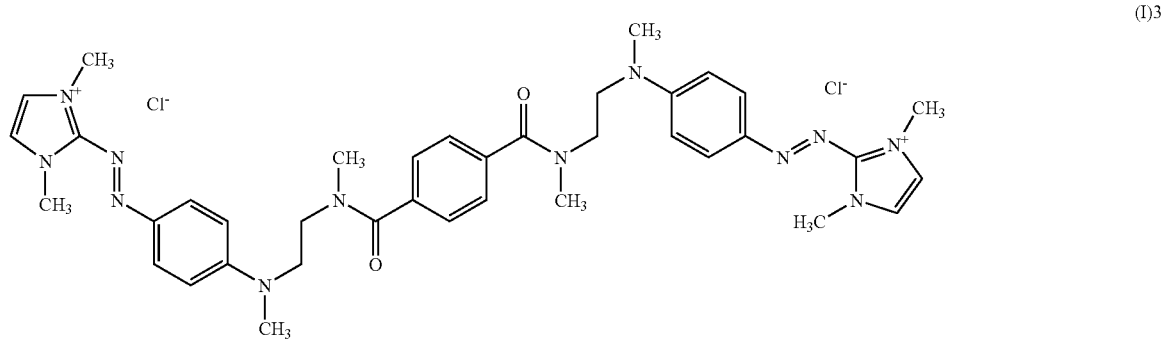

(I)3

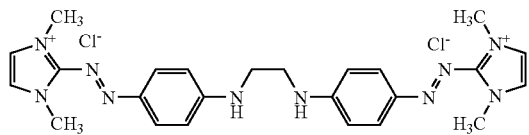 (I)4

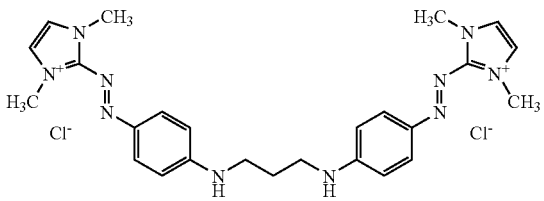 (I)5

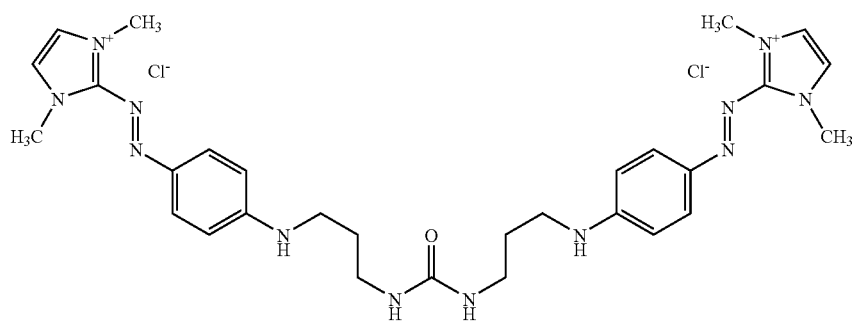 (I)6

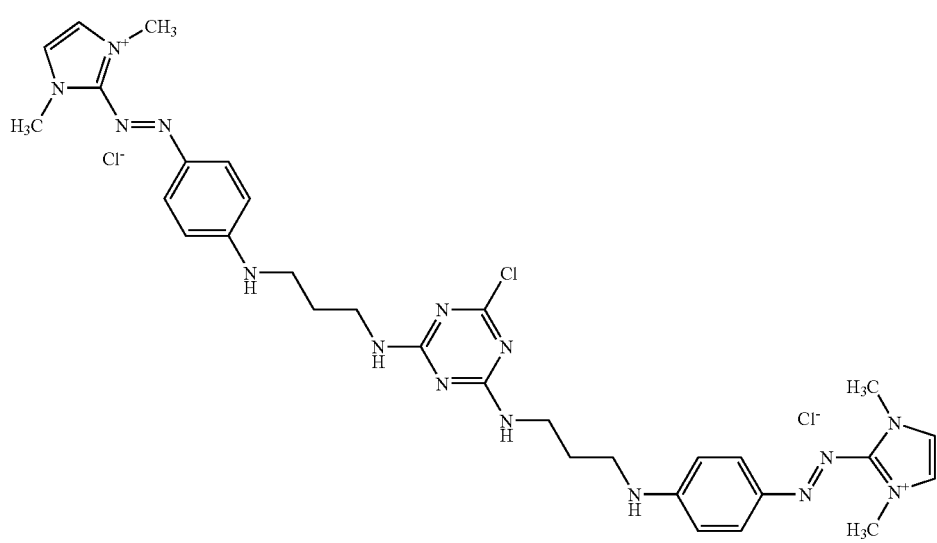 (I)7

According to the present invention, among the compounds of formula (III) that may be mentioned more particularly is the compound sold by the company CIBA under the name Pergasol Orange F-3G, having the following formula:

According to the present invention, among the compounds of formula (IV) that may be mentioned more particularly is the compound sold by the company Ciba under the name Pergasol Jaune F-6G, having the following formula:

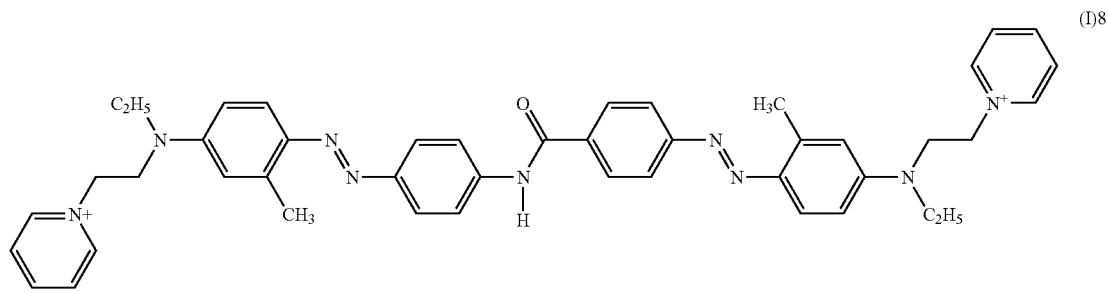 (I)8

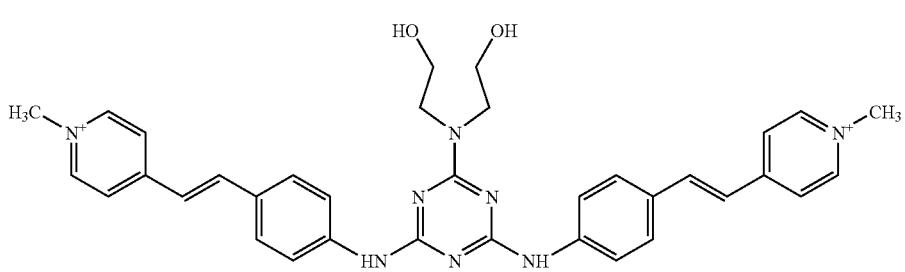

(I)9

The dyes of formula (I), (II), (III) and (IV) according to the present invention are known per se, and are described and prepared in patents EP-0 318 294 B1 or U.S. Pat. No. 5,674,299 or U.S. Pat. No. 5,708,151, the content of which forms an integral part of the present invention.

They are generally present in the dye composition in proportions ranging from about 0.01% to 40% and preferably from about 0.1% to 20% by weight relative to the total weight of the composition.

Direct Dyes

The direct dyes that may be used according to the invention may be chosen, in a nonlimiting manner, for example, from neutral, acidic or cationic nitrobenzene direct dyes, neutral, acidic or cationic azo direct dyes, cationic direct dyes comprising a quaternized nitrogen atom and a —CH=N— bond, quinone direct dyes and in particular, neutral, acidic or cationic anthraquinones, azine direct dyes, triarylmethane direct dyes, indoamine direct dyes and natural direct dyes.

Among the benzene direct dyes that may be used according to the invention, mention may be made especially of the following compounds:

1,4-diamino-2-nitrobenzene
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene Among the azo direct dyes that may be used according to the invention, mention may be made of the cationic azo dyes described in patent applications WO 95/15144, WO 95/01772 and EP 714 954, the content of which forms an integral part of the invention.

Among these compounds, mention may be made most particularly of the following dyes:

1-,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned are the following dyes described in the Colour Index International 3rd edition:

Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-[bis(β-hydroxy-ethyl)amino]benzene and 4-hydroxy-3-(2-methoxyphenylazo)-1-naphthalenesulfonic acid.

Among the quinone direct dyes that may be mentioned are the following dyes:

Disperse Red 15
Solvent Violet 13
Acid Violet 43
Disperse Violet 1
Disperse Violet 4

Disperse Blue 1
Disperse Violet 8
Disperse Blue 3
Disperse Red 11
Acid Blue 62
Disperse Blue 7
Basic Blue 22
Disperse Violet 15
Basic Blue 99 and also the following compounds:
  1-N-methylmorpholiniumpropylamino-4-hydroxyanthraquinone
  1-aminopropylamino-4-methylaminoanthraquinone
  1-aminopropylaminoanthraquinone
  5-β-hydroxyethyl-1,4-diaminoanthraquinone
  2-aminoethylaminoanthraquinone
  1,4-bis(β, γ-dihydroxypropylamino)anthraquinone Among the azine dyes that may be mentioned are the following compounds:
  Basic Blue 17
  Basic Red 2.

Among the triarylmethane dyes that may be used according to the invention, mention may be made of the following compounds:
  Basic Green 1
  Acid Blue 9
  Basic Violet 3
  Basic Violet 14
  Basic Blue 7
  Acid Violet 49
  Basic Blue 26
  Acid Blue 7

Among the indoamine dyes that may be used according to the invention, mention may be made of the following compounds:
  2-β-hydroxyethylamino-5-[bis(β-4'-hydroxyethyl)amino]-anilino-1,4-benzoquinone;
  2-β-hydroxyethylamino-5-(2'-methoxy-4'-amino)anilino-1,4-benzoquinone;
  3-N(2'-chloro-4'-hydroxy)phenylacetylamino-6-methoxy-1,4-benzoquinoneimine;
  3-N(3'-chloro-4'-methylamino)phenylureido-6-methyl-1,4-benzoquinoneimine;
  3-[4'-N-(ethylcarbamylmethyl)amino]phenylureido-6-methyl-1,4-benzoquinoneimine.

Among the direct cationic dyes comprising a quaternized nitrogen atom and a —CH=N— bond, mention may be made of the compounds described in patent U.S. Pat. No. 5,980,587 and especially those of the following formulae:

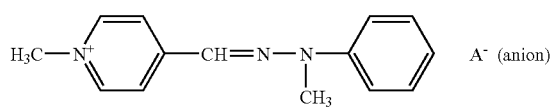

i.e. (1-methyl-1-phenyl)-2(1-methine-4N-methylpyridinylium)hydrazine, chloride or methyl sulfate

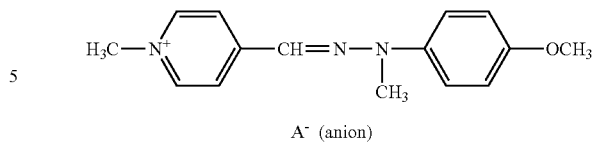

i.e. (1-methyl-1-paramethoxyphenyl)-2(1-methine-4N-methylpyridinylium)hydrazine, chloride or methyl sulfate.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, and especially henna-based poultices or extracts.

The direct dye(s) preferably represent(s) from 0.001% to 20% by weight approximately, and even more preferably from 0.005% to 10% by weight approximately, relative to the total weight of the composition.

The medium of the composition that is suitable for dyeing is preferably an aqueous medium consisting of water and may advantageously contain cosmetically acceptable organic solvents including, more particularly, alcohols such as ethyl alcohol, isopropyl alcohol, benzyl alcohol and phenylethyl alcohol, or glycols or glycol ethers such as, for example, ethylene glycol monomethyl, monoethyl and monobutyl ethers, propylene glycol or its ethers such as, for example, propylene glycol monomethyl ether, butylene glycol, dipropylene glycol and diethylene glycol alkyl ethers such as, for example, diethylene glycol monoethyl ether or monobutyl ether. The solvents may then be present in concentrations of between about 0.5% and 20% and preferably between about 2% and 10% by weight relative to the total weight of the composition.

The dye composition may also contain an effective amount of other agents that are previously known elsewhere for direct dyeing, such as various common adjuvants, for instance surfactants that are well known in the prior art and of anionic, cationic, nonionic, amphoteric or zwitterionic type or mixtures thereof, thickeners, antioxidants, fragrances, dispersants, conditioners, especially including cationic or amphoteric nonionic polymers, opacifiers, sequestering agents such as EDTA and etidronic acid, UV-screening agents, waxes, volatile or nonvolatile, cyclic, linear or branched silicones, which are possibly organomodified (especially with amine groups), preserving agents, ceramides, pseudoceramides, plant, mineral or synthetic oils, vitamins or provitamins, for instance panthenol, and nonionic, anionic, amphoteric or cationic associative polymers.

Associative Polymers

Associative polymers are water-soluble polymers capable, in an aqueous medium, of reversibly associating with each other or with other molecules.

Their chemical structure comprises hydrophilic zones and hydrophobic zones characterized by at least one fatty chain.

Associative Polymers of Anionic Type:
  Among these, mention may be made of:
  (I) those comprising at least one hydrophilic unit and at least one fatty-chain allyl ether unit, more particularly those whose hydrophilic unit consists of an ethylenic unsaturated anionic monomer, more particularly a vinylcarboxylic acid and most particularly an acrylic acid or a methacrylic acid or mixtures thereof, the fatty-chain allyl ether unit of which corresponding to the monomer of formula (I) below:

$$CH_2=CR'CH_2OB_nR \qquad (I)$$

in which R' denotes H or $CH_3$, B denotes an ethyleneoxy radical, n is zero or denotes an integer ranging from 1 to 100, R denotes a hydrocarbon-based radical chosen from alkyl, arylalkyl, aryl, alkylaryl and cycloalkyl radicals, containing from 8 to 30 carbon atoms, preferably 10 to 24 carbon atoms and even more particularly from 12 to 18 carbon atoms. A unit of formula (I) that is more particularly preferred is a unit in which R' denotes H, n is equal to 10 and R denotes a stearyl ($C_{18}$) radical.

Anionic associative polymers of this type are described and prepared, according to an emulsion polymerization process, in patent EP-0 216 479.

Among these anionic associative polymers that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a well-known copolymerizable unsaturated polyethylenic monomer, for instance diallyl phthalate, allyl(meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), in particular those sold by the company Allied Colloids under the names Salcare SC 80® and Salcare SC 90®, which are aqueous 30% emulsions of a crosslinked terpolymer of methacrylic acid, of ethyl acrylate and of steareth-10 allyl ether (40/50/10).

(II) those comprising at least one hydrophilic unit of unsaturated olefinic carboxylic acid type, and at least one hydrophobic unit of ($C_{10}$–$C_{30}$)alkyl ester of unsaturated carboxylic acid type.

Preferably, these polymers are chosen from those in which the hydrophilic unit of unsaturated olefinic carboxylic acid type corresponds to the monomer of formula (II) below:

in which $R_1$ denotes H or $CH_3$ or $C_2H_5$, that is to say acrylic acid, methacrylic acid or ethacrylic acid units, and in which the hydrophobic unit of ($C_{10}$–$C_{30}$)alkyl ester of unsaturated carboxylic acid type corresponds to the monomer of formula (III) below:

in which $R_2$ denotes H or $CH_3$ or $C_2H_5$ (that is to say acrylate, methacrylate or ethacrylate units) and preferably H (acrylate units) or $CH_3$ (methacrylate units), $R_3$ denoting a $C_{10}$–$C_{30}$ and preferably $C_{12}$–$C_{22}$ alkyl radical.

($C_{10}$–$C_{30}$) alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among the anionic associative polymers of this type that will be used more particularly are polymers formed from a monomer mixture comprising:

(i) essentially acrylic acid,
(ii) an ester of formula (III) described above in which $R_2$ denotes H or $CH_3$, $R_3$ denoting an alkyl radical containing from 12 to 22 carbon atoms,
(iii) and a crosslinking agent, which is a well-known copolymerizable polyethylenic unsaturated monomer, for instance diallyl phthalate, allyl (meth)acrylate, divinylbenzene, (poly)ethylene glycol dimethacrylate and methylenebisacrylamide.

Among anionic associative polymers of this type that will be used more particularly are those consisting of from 95% to 60% by weight of acrylic acid (hydrophilic unit), 4% to 40% by weight of $C_{10}$–$C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}$–$C_{30}$ alkyl acrylate (hydrophobic unit) and 0.1% to 0.6% by weight of crosslinking polymerizable monomer such as those described above.

Among said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

(III) maleic anhydride/$C_{30}$–$C_{38}$ α-olefin/alkyl maleate terpolymers, such as the product (maleic anhydride/$C_{30}$–$C_{38}$ α-olefin/isopropyl maleate copolymer) sold under the name Performa V 1608® by the company Newphase Technologies.

(IV) acrylic terpolymers comprising:
(a) about 20% to 70% by weight of a carboxylic acid containing α,β-monoethylenic unsaturation,
(b) about 20% to 80% by weight of a non-surfactant monomer containing α,β-monoethylenic unsaturation other than (a),
(c) about 0.5% to 60% by weight of a nonionic monourethane which is the product of reaction of a monohydric surfactant with a monoisocyanate containing monoethylenic unsaturation, such as those described in patent application EP-A-0 173 109 and more particularly the terpolymer described in Example 3, namely a methacrylic acid/methyl acrylate/behenyl dimethyl-meta-isopropenylbenzylisocyanate ethoxylated (40 EO) terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

Preferentially, these compounds also comprise as monomer an ester of a carboxylic acid containing α,β-monoethylenic unsaturation and of a $C_1$–$C_4$ alcohol.

An example of a compound of this type which may be mentioned is Aculyn 22® sold by the company Rohm & Haas, which is a methacrylic acid/ethyl acrylate/stearyl methacrylate oxyalkylenated terpolymer.

Associative Polymers of Cationic Type

According to the present invention, they are preferably chosen from quaternized cellulose derivatives and polyacrylates containing non-cyclic amino side groups.

The quaternized cellulose derivatives are in particular:
quaternized celluloses modified with groups comprising at least one fatty chain, such as alkyl, arylalkyl or alkylaryl groups containing at least 8 carbon atoms, or mixtures thereof,
quaternized hydroxyethylcelluloses modified with groups comprising at least one fatty chain, such as alkyl, arylalkyl or alkylaryl groups containing at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethyl-celluloses containing $C_8$–$C_{30}$ fatty chains that may be mentioned include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol, and the products Crodacel QM, Crodacel QL ($C_{12}$ alkyl) and Crodacel QS ($C_{18}$ alkyl) sold by the company Croda.

Amphoteric Associative Polymers

These are preferably chosen from polymers comprising at least one non-cyclic cationic unit. Even more particularly, the ones that are preferred are those prepared from or comprising 1 to 20 mol % of monomer comprising a fatty chain, preferably 1.5 to 15 mol % and even more particularly 1.5 to 6 mol %, relative to the total number of moles of monomers.

The amphoteric associative polymers that are preferred according to the invention comprise, or are prepared by copolymerizing:

1) at least one monomer of formula (Ia) or (Ib):

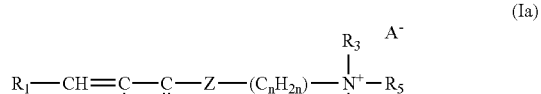

(Ia)

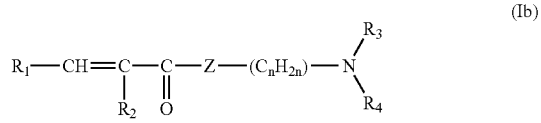

(Ib)

in which $R_1$ and $R_2$, which may be identical or different, represent a hydrogen atom or a methyl radical, $R_3$, $R_4$ and $R_5$, which may be identical or different, represent a linear or branched alkyl radical containing from 1 to 30 carbon atoms, Z represents an NH group or an oxygen atom, n is an integer from 2 to 5, $A^-$ is an anion derived from an organic or mineral acid, such as a methosulfate anion or a halide such as chloride or bromide;

2) at least one monomer of formula (II)

(II)

in which $R_6$ and $R_7$, which may be identical or different, represent a hydrogen atom or a methyl radical; and 3) at least one monomer of formula (III):

(III)

in which $R_6$ and $R_7$, which may be identical or different, represent a hydrogen atom or a methyl radical, X denotes an oxygen or nitrogen atom and $R_8$ denotes a linear or branched alkyl radical containing from 1 to 30 carbon atoms; at least one of the monomers of formula (Ia), (Ib) or (III) comprising at least one fatty chain.

The monomers of formulae (Ia) and (Ib) of the present invention are preferably chosen from the group consisting of:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quaternized, for example with a $C_3$–$C_4$ alkyl halide or a $C_1$–$C_4$ dialkyl sulfate.

More particularly, the monomer of formula (Ia) is chosen from acrylamidopropyltrimethylammonium chloride and methacrylamidopropyltrimethylammonium chloride.

The monomers of formula (II) of the present invention are preferably chosen from the group consisting of acrylic acid, methacrylic acid, crotonic acid and 2-methylcrotonic acid. More particularly, the monomer of formula (II) is acrylic acid.

The monomers of formula (III) of the present invention are preferably chosen from the group consisting of $C_{12}$–$C_{22}$ and more particularly $C_{16}$–$C_{18}$ alkyl acrylates or methacrylates.

The monomers constituting the fatty-chain amphoteric polymers of the invention are preferably already neutralized and/or quaternized.

The ratio of the number of cationic charges/anionic charges is preferably equal to about 1.

The amphoteric associative polymers according to the invention preferably comprise from 1 mol % to 10 mol % of the monomer comprising a fatty chain (monomer of formula (Ia), (Ib) or (III)), and preferably from 1.5 mol % to 6 mol %.

The weight-average molecular weights of the amphoteric associative polymers according to the invention may range from 500 to 50 000 000 and are preferably between 10 000 and 5 000 000.

The amphoteric associative polymers according to the invention may also contain other monomers such as nonionic monomers and in particular such as $C_1$–$C_4$ alkyl acrylates or methacrylates.

Amphoteric associative polymers are described and prepared, for example, in patent application WO 98/44012.

Among the amphoteric associative polymers according to the invention, the ones that are preferred are acrylic acid/(meth)acrylamidopropyltrimethylammonium chloride/stearyl methacrylate terpolymers.

Associative Polymers of Nonionic Type

According to the invention, these are preferably chosen from:
(1) celluloses modified with groups comprising at least one fatty chain;
  examples that may be mentioned include:
    hydroxyethylcelluloses modified with groups comprising at least one fatty chain, such as alkyl, arylalkyl or alkylaryl groups, or mixtures thereof, and in which the alkyl groups are preferably $C_8$–$C_{22}$, for instance the product Natrosol Plus Grade 330 CS® ($C_{16}$ alkyls) sold by the company Aqualon, or the product Bermocoll EHM 100® sold by the company Berol Nobel,
    those modified with alkylphenyl polyalkylene glycol ether groups, such as the product Amercell Polymer HM-1500® (nonylphenyl polyethylene glycol (15) ether) sold by the company Amerchol.
(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc.
(3) copolymers of vinylpyrrolidone and of fatty-chain hydrophobic monomers; examples that may be mentioned include:
    the products Antaron V216® or Ganex V216® (vinylpyrrolidone/hexadecene copolymer) sold by the company I.S.P.
    the products Antaron V220® or Ganex V220® (vinylpyrrolidone/eicosene copolymer) sold by the company I.S.P.
(4) copolymers of $C_1$–$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.
(5) copolymers of hydrophilic methacrylates or acrylates and of hydrophobic monomers comprising at least one fatty chain, such as, for example, the polyethylene glycol methacrylate/lauryl methacrylate copolymer.
(6) polyurethane polyethers comprising in their chain both hydrophilic blocks usually of polyoxyethylenated nature and hydrophobic blocks which may be aliphatic sequences alone and/or cycloaliphatic and/or aromatic sequences.
(7) polymers with an aminoplast ether skeleton containing at least one fatty chain, such as the Pure Thix® compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethylenated chain comprising from 50 to 1 000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, mention may also be made of Rheolate 205® containing a urea function, sold by the company Rheox, or the Rheolates® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used according to the invention are in particular those described in the article by G. Fonnum, J. Bakke and Fk. Hansen—Colloid Polym. Sci 271, 380.389 (1993).

Even more particularly, according to the invention, it is preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl-isocyanate) (SMDI), at 35% by weight in a mixture of propylene glycol (39%) and water (26%)].

The associative polymers of nonionic, anionic, cationic or amphoteric type are preferably used in an amount that may vary from about 0.1% to 10% by weight relative to the total weight of the dyeing composition. More preferably, this amount varies from about 0.5% to 5% by weight, and even more preferably from about 1% to 3% by weight.

Cationic Polymers

For the purposes of the present invention, the term "cationic polymer" denotes any polymer containing cationic groups and/or groups that may be ionized into cationic groups.

The cationic polymers that may be used in accordance with the present invention may be chosen from all those already known per se as improving the cosmetic properties of the hair, i.e. especially those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or may be borne by a side substituent directly attached thereto.

The cationic polymers used generally have a number-average molecular mass of between 500 and $5 \times 10^6$ approximately and preferably between $10^3$ and $3 \times 10^6$ approximately.

Among the cationic polymers that may be mentioned more particularly are polymers of the polyamine, polyamino amide and polyquaternary ammonium type.

These are known products. They are described in particular in French patents Nos. 2 505 348 and 2 542 997. Among said polymers, mention may be made of:

(1) homopolymers or copolymers derived from acrylic or methacrylic esters or amides and comprising at least one of the units of formula (I), (II), (III) or (IV) below:

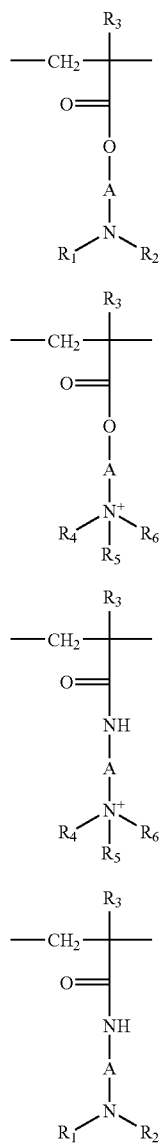

in which:
  R₃, which may be identical or different, denote a hydrogen atom or a CH₃ radical;
  A, which may be identical or different, represent a linear or branched alkyl group of 1 to 6 carbon atoms, preferably 2 or 3 carbon atoms, or a hydroxyalkyl group of 1 to 4 carbon atoms;
  R₄, R₅ and R₆, which may be identical or different, represent an alkyl group containing from 1 to 18 carbon atoms or a benzyl radical and preferably an alkyl group containing from 1 to 6 carbon atoms;
  R₁ and R₂, which may be identical or different, represent hydrogen or an alkyl group containing from 1 to 6 carbon atoms, and preferably methyl or ethyl;
  X denotes an anion derived from an inorganic or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$–$C_4$) alkyls, acrylic or methacrylic acids or esters thereof, vinyllactams such as vinylpyrrolidone or vinylcaprolactam, and vinyl esters.

Thus, among these polymers of family (1), mention may be made of:
  copolymers of acrylamide and of dimethylaminoethyl methacrylate quaternized with dimethyl sulfate or with a dimethyl halide, such as the product sold under the name Hercofloc® by the company Hercules,
  the copolymers of acrylamide and of methacryloyloxyethyltrimethylammonium chloride described, for example, in patent application EP-A-080 976 and sold under the name Bina Quat P 100® by the company Ciba Geigy,
  the copolymer of acrylamide and of methacryloyloxyethyltrimethylammonium methosulfate sold under the name Reten® by the company Hercules,
  quaternized or non-quaternized vinylpyrrolidone/dialkylaminoalkyl acrylate or methacrylate copolymers, such as the products sold under the name "Gafquat®" by the company ISP, such as, for example, "Gafquat® 734" or "Gafquat® 755", or alternatively the products known as "Copolymer® 845, 958 and 937". These polymers are described in detail in French patents 2 077 143 and 2 393 573,
  dimethylaminoethyl methacrylate/vinylcaprolactam/-vinylpyrrolidone terpolymers, such as the product sold under the name Gaffix® VC 713 by the company ISP,
  vinylpyrrolidone/methacrylamidopropyldimethylamine copolymers sold in particular under the name Styleze® CC 10 by ISP, and quaternized vinylpyrrolidone/dimethylaminopropyl methacrylamide copolymers such as the product sold under the name "Gafquat® HS 100" by the company ISP.

(2) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, as well as the oxidation and/or quaternization products of these polymers. Such polymers are described, in particular, in French patents 2 162 025 and 2 280 361.

(3) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(4) The polyamino amide derivatives resulting from the condensation of polyalkylene polyamines with polycarboxylic acids followed by alkylation with difunctional agents. Mention may be made, for example, of adipic acid/dialkylaminohydroxyalkyl-dialkylenetriamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylamino-hydroxypropyl/diethylenetriamine polymers sold under the name "Cartaretine® F, F4 or F8" by the company Sandoz.

(5) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett® 57" by the company Hercules Inc. or alternatively under the name "PD 170®" or "Delsette® 101" by the company Hercules in the case of the adipic acid/epoxypropyl/diethylenetriamine copolymer.

(6) Cyclopolymers of alkyldiallylamine or of dialkyldiallylammonium, such as the homopolymers or copolymers containing, as main constituent of the chain, units corresponding to formula (V) or (VI):

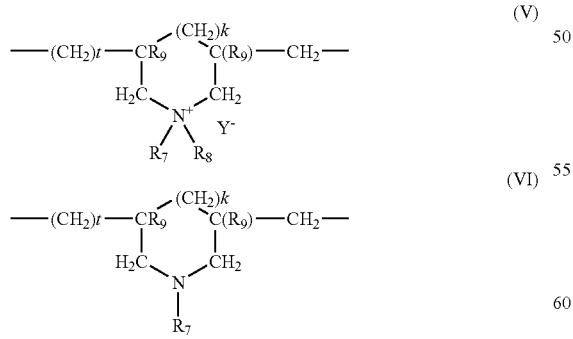

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 22 carbon atoms, a hydroxyalkyl group in which the alkyl group preferably has 1 to 5 carbon atoms, a lower ($C_1$–$C_4$) amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group having from 1 to 4 carbon atoms; $Y^-$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may be made more particularly of the dimethyldiallylammonium chloride homopolymer sold under the name "Merquat® 100" by the company Calgon (and its homologs of low weight-average molecular mass) and the copolymers of diallyldimethylammonium chloride and of acrylamide, sold under the name "Merquat® 550".

(7) The quaternary diammonium polymer containing repeating units corresponding to the formula:

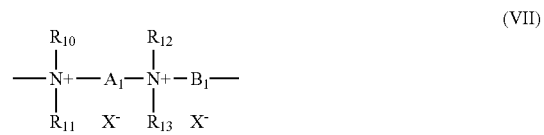

in which formula (VII):

$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$–$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO-D-OC—$(CH_2)_n$— in which n is between 1 and 100 and preferably between 1 and 50, and D denotes:

a) a glycol residue of formula: —O-Z-O—, where Z denotes a linear or branched hydrocarbon-based radical or a group corresponding to one of the following formulae:

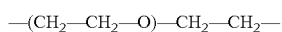

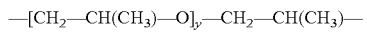

where x and y denote an integer from 1 to 4, representing a defined and unique degree of polymerization or any number from 1 to 4 representing an average degree of polymerization;

b) a bis-secondary diamine residue such as a piperazine derivative;
c) a bis-primary diamine residue of formula: —NH—Y—NH—, where Y denotes a linear or branched hydrocarbon-based radical, or alternatively the divalent radical

—CH$_2$—CH$_2$—S—S—CH$_2$—CH$_2$—;

d) a ureylene group of formula: —NH—CO—NH—.

Preferably, X_ is an anion such as chloride or bromide.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to the following formula (VIII):

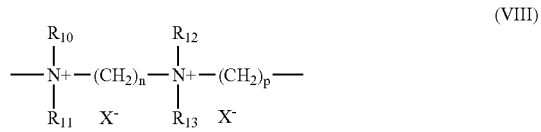

(VIII)

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and X— is an anion derived from an inorganic or organic acid.

(8) Polyquaternary ammonium polymers consisting of units of formula (IX)

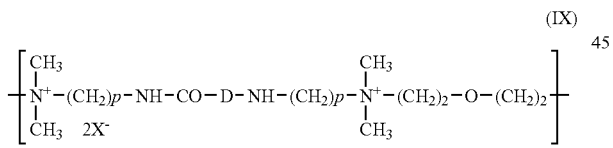

(IX)

in which:
p denotes an integer ranging from 1 to 6 approximately,
D may be nothing or may represent a group —(CH$_2$)$_r$—CO— in which
r denotes a number equal to 4 or 7, and
$X^-$ is an anion derived from a mineral or organic acid.

The cationic polymers comprising units of formula (IX) are described especially in patent application EP-A-122 324 and may be prepared according to the processes described in U.S. Pat. Nos. 4,157,388, 4,390,689, 4,702,906 and 4,719,282.

Among these polymers, the ones that are preferred are those with a molecular mass, measured by carbon-13 NMR of less than 100 000, and in the formula of which:
p is equal to 3, and a) D represents a —(CH$_2$)$_4$—CO— group, X denotes a chlorine atom, the molecular mass measured by carbon-13 NMR ($^{13}$C NMR) being about 5 600;
a polymer of this type is sold by the company Miranol under the name Mirapol-AD1,
b) D represents a —(CH$_2$)$_7$—CO— group, X denotes a chlorine atom, the molecular mass measured by carbon-13 NMR ($^{13}$C NMR) being about 8 100; a polymer of this type is sold by the company Miranol under the name Mirapol-AZ1,
c) D denotes the value zero, X denotes a chlorine atom, the molecular mass measured by carbon-13 NMR ($^{13}$C NMR) being about 25 500; a polymer of this type is sold by the company Miranol under the name Mirapol-A15,
d) a "Block Copolymer" formed from units corresponding to the polymers described in paragraphs a) to c), sold by the company Miranol under the names Mirapol-9 ($^{13}$C NMR molecular mass, about 7 800), Mirapol-175 ($^{13}$C NMR molecular mass, about 8 000) and Mirapol-95 ($^{13}$C NMR molecular mass, about 12 500).

The polymer containing units of formula (IX) in which p is equal to 3, D denotes the value zero and X denotes a chlorine atom, the molecular mass measured by carbon-13 NMR ($^{13}$C NMR) being about 25 500, is even more particularly preferred according to the invention.

(9) Quaternary polymers of vinylpyrrolidone and of vinylimidazole, such as, for example, the products sold under the names Luviquat FC 905, FC 550 and FC 370 by the company BASF.

(10) Polyamines such as Polyquart H sold by Henkel, which is given under the reference name "Polyethylene glycol (15) tallow polyamine" in the CTFA dictionary.

(11) Crosslinked methacryloyloxy(C$_1$–C$_4$) alkyltri (C$_1$–C$_4$)-alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of said copolymer in mineral oil can be used more particularly. This dispersion is sold under the name "Salcare® SC 92" by the company Allied Colloids. A crosslinked meth-acryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which may be used in the context of the present invention, it is preferred to use the polymers of families (1), (6), (7), (8) and (11) and even more preferably the polymers containing repeating units of formulae (W) and (U) below:

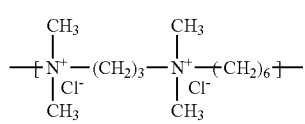

(W)

and in particular those whose molecular weight, determined by gel permeation chromatography, is between 9500 and 9900;

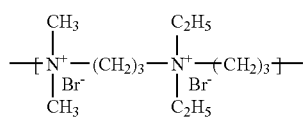

(U)

and in particular those whose molecular weight, determined by gel permeation chromatography, is about 1200.

The concentration of cationic polymer in the composition according to the present invention may range from 0.01% to 10% by weight relative to the total weight of the composition, preferably from 0.05% to 5% and even more preferably from 0.1% to 3%.

Amphoteric Polymers

The amphoteric polymers that may be used in accordance with the present invention may be chosen from polymers comprising units K and M randomly distributed in the polymer chain, in which K denotes a unit derived from a monomer comprising at least one basic nitrogen atom and M denotes a unit derived from an acidic monomer comprising one or more carboxylic or sulfonic groups, or alternatively K and M may denote groups derived from zwitterionic carboxybetaine or sulfobetaine monomers;

K and M may also denote a cationic polymer chain comprising primary, secondary, tertiary or quaternary amine groups, in which at least one of the amine groups bears a carboxylic or sulfonic group linked via a hydrocarbon-based radical, or alternatively K and M form part of a chain of a polymer containing an α,β-dicarboxylic ethylene unit in which one of the carboxylic groups has been made to react with a polyamine comprising one or more primary or secondary amine groups.

The amphoteric polymers corresponding to the above definition that are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and from a substituted vinyl compound containing at least one basic atom, such as, more particularly, dialkylaminoalkyl methacrylate and acrylate, dialkylaminoalkylmethacrylamide and -acrylamide. Such compounds are described in U.S. Pat. No. 3,836,537. Mention may also be made of the sodium acrylate/acrylamidopropyltrimethylammonium chloride copolymer sold under the name Polyquart KE 3033 by the company Henkel.

The substituted vinyl compound containing at least one basic atom may also be a dialkyldiallylammonium salt such as dimethyldiallylammonium chloride. The copolymers of acrylic acid and of the latter monomer are sold under the names Merquat 280, Merquat 295 and Merquat Plus 3330 by the company Calgon.

(2) Polymers containing units derived from:

a) at least one monomer chosen from acrylamides and methacrylamides substituted on the nitrogen with an alkyl radical, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is Octylacrylamide/acrylates/butylaminoethyl methacrylate copolymer such as the products sold under the name Amphomer or Lovocryl 47 by the company National Starch are particularly used.

(3) Polyamino amides that are crosslinked and alkylated partially or totally derived from polyamino amides of general formula:

(X)

in which $R_{19}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of said acids to a bis(primary) or bis(secondary) amine, and Z denotes a bis(primary), mono- or bis(secondary) polyalkylene-polyamine radical and preferably represents:

a) in proportions of from 60 to 100 mol %, the radical

(XI)

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (XI) above in which x=2 and p=1 and which is derived from ethylenediamine, or the radical derived from piperazine:

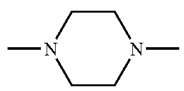

c) in proportions of from 0 to 20 mol %, the —NH—(CH$_2$)$_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic acid, methacrylic acid and itaconic acid.

The alkane sultones used in the alkylation are preferably propane sultone or butane sultone, and the salts of the alkylating agents are preferably the sodium or potassium salts.

(4) Polymers containing zwitterionic units of formula:

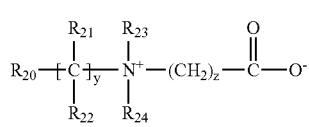

(XII)

in which R$_{20}$ denotes a polymerizable unsaturated group such as an acrylate, methacrylate, acrylamide or methacrylamide group, y and z represent an integer from 1 to 3, R$_{21}$ and R$_{22}$ represent a hydrogen atom, methyl, ethyl or propyl, R$_{23}$ and R$_{24}$ represent a hydrogen atom or an alkyl radical such that the sum of the carbon atoms in R$_{23}$ and R$_{24}$ does not exceed 10.

The polymers comprising such units can also contain units derived from nonzwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of butyl methacrylate/dimethyl carboxymethylammonio ethyl methacrylate such as the product sold under the name Diaformer Z301 by the company Sandoz.

(5) Polymers derived from chitosan, described especially in French patent No 2 137 684 or U.S. Pat. No. 3,879,376, containing monomer units corresponding to formulae (XIII), (XIV) and (XV) below connected in their chain:

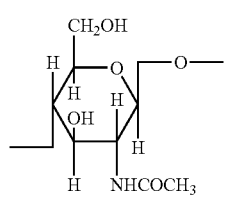

(XIII)

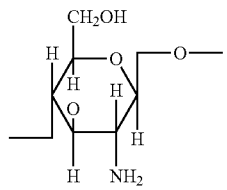

(XIV)

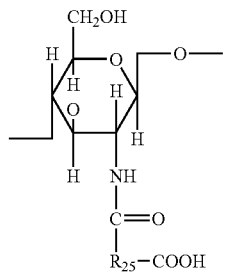

(XV)

the unit (XIII) being present in proportions of between 0 and 30%, the unit (XIV) in proportions of between 5 and 50% and the unit (XV) in proportions of between 30 and 90%, it being understood that, in this unit (XV), R$_{25}$ represents a radical of formula:

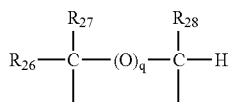

in which q denotes zero or 1;
if q=0, R$_{26}$, R$_{27}$ and R$_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the radicals R$_{26}$, R$_{27}$ and R$_{28}$ being, in this case, a hydrogen atom;
or, if q=1, R$_{26}$, R$_{27}$ and R$_{28}$ each represent a hydrogen atom, as well as the salts formed by these compounds with bases or acids.

More particularly preferred polymers of this type comprise from 0 to 20% by weight of the units (XIII), from 40 to 50% by weight of units (XIV), and from 40 to 50% by weight of units (XV) in which R$_{25}$ denotes the radical —CH$_2$—CH$_2$—;

(6) Polymers derived from the N-carboxyalkylation of chitosan, such as N-carboxymethylchitosan or N-carboxybutylchitosan sold under the name "Evalsan" by the company Jan Dekker.

(7) Polymers corresponding to the general formula (XI) as described, for example, in French patent 1 400 366:

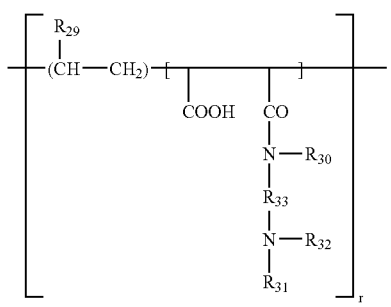 (XVI)

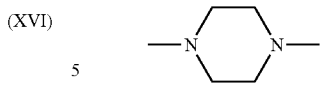 (XVI)

in which $R_{29}$ represents a hydrogen atom, a $CH_{3O}$, $_{CH_3}CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: —$R_{33}$—$N(R_{31})_2$, $R_{33}$ representing a —$CH_2$—$CH_2$—, —$CH_2$—$CH_2$—$CH_2$— or —$CH_2$—$CH(CH_3)$— group, $R_{31}$ having the meanings mentioned above, as well as the higher homologs of these radicals and containing up to 6 carbon atoms, r is such that the molecular weight is between 500 and 6 000 000 and preferably between 1000 and 1 000 000.

(8) Amphoteric polymers of the type -D-X-D-X— chosen from:

a) polymers obtained by the action of chloroacetic acid or sodium chloroacetate on compounds containing at least one unit of formula:

-D-X-D-X-D- (XVII)

where D denotes a radical

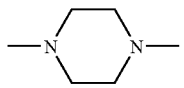

and X denotes the symbol E or E', E or E', which may be identical or different, denotes a divalent radical which is an alkylene radical with a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

-D-X-D-X— (XVIII)

where D denotes a radical and X denotes the symbol E or E' and at least once E'; E having the meaning given above and E' being a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$–$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The amphoteric polymers that are particularly preferred according to the invention are those of family (1).

According to the invention, the amphoteric polymer(s) may represent from 0.01% to 10% by weight, preferably from 0.05% to 5% by weight and even more preferably from 0.1% to 3% by weight relative to the total weight of the composition.

The compositions of the invention preferably comprise one or more surfactants which can be chosen without preference, alone or as mixtures, from anionic, amphoteric, nonionic, zwitterionic and cationic surfactants.

The surfactants that are suitable for carrying out the present invention are, in particular, the following:

(i) Anionic Surfactant(s):

As examples of anionic surfactants which can be used, alone or as mixtures, in the context of the present invention, mention may be made in particular (nonlimiting list) of salts (in particular alkaline salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$–$C_{24}$)alkyl sulfosuccinates, ($C_6$–$C_{24}$)alkyl ether sulfosuccinates, ($C_6$–$C_{24}$)alkylamide sulfosuccinates; ($C_6$–$C_{24}$)alkyl sulfoacetates; ($C_6$–$C_{24}$) acyl sarcosinates and ($C_6$–$C_{24}$)acyl glutamates. It is also possible to use the carboxylic esters of ($C_6$–$C_{24}$)alkylpolyglycosides, such as alkylglucoside citrates, alkylpolyglycoside tartrates and alkylpolyglycoside sulfosuccinates, alkylsulfosuccinamates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Alkyl-D-galactosideuronic acids and their salts, polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and their salts, in particular those containing from 2 to 50 alkylene oxide, in particular ethylene oxide, groups, and mixtures thereof can also be used.

(ii) Nonionic Surfactant(s):

The nonionic surfactants are also compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (nonlimiting list) polyethoxylated or polypropoxylated alkylphenols, α-diols or alcohols having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric or Zwitterionic Surfactant(s):

The amphoteric or zwitterionic surfactants, whose nature is not a critical feature in the context of the present invention, can be, in particular (nonlimiting list), aliphatic secondary or tertiary amine derivatives in which the aliphatic radical is a linear or branched chain containing 8 to 18 carbon atoms and containing at least one water-soluble anionic group (for example carboxylate, sulfonate, sulfate, phosphate or phosphonate); mention may also be made of ($C_8$–$C_{20}$)alkylbetaines, sulfobetaines, ($C_8$–$C_{20}$) alkylamido ($C_1$–$C_6$) alkylbetaines or ($C_8$–$C_{20}$) alkylamido ($C_1$–$C_6$) alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names amphocarboxyglycinates and amphocarboxypropionates of respective structures:

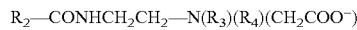

in which: $R_2$ denotes an alkyl radical of an acid $R_2$—COOH present in hydrolyzed coconut oil, a heptyl, nonyl or undecyl radical, $R_3$ denotes a β-hydroxyethyl group and $R_4$ denotes a carboxymethyl group; and

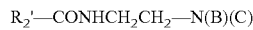

in which:

B represents —$CH_2CH_2OX'$, C represents —$(CH_2)_z$—Y', with z=1 or 2,

X' denotes a —$CH_2CH_2$—COOH group or a hydrogen atom,

Y' denotes —COOH or a —$CH_2$—CHOH—$SO_3H$ radical, $R_2'$ denotes an alkyl radical of an acid $R_9$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caryloamphodipropionate, lauroamphodipropionic acid and cocoamphodipropionic acid.

By way of example, mention may be made of the cocoamphodiacetate sold under the trade name Miranolo C2M Concentrate by the company Rhodia Chimie.

(iv) Cationic Surfactants:

Among the cationic surfactants that may be mentioned in particular (nonlimiting list) are: primary, secondary or tertiary fatty amine salts, optionally polyoxyalkylenated; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of surfactants present in the composition according to the invention can range from 0.01% to 40% and preferably from 0.5% to 30% relative to the total weight of the composition.

Needless to say, a person skilled in the art will take care to select the optional additional compound(s) mentioned above such that the advantageous properties intrinsically associated with the dye composition according to the invention are not, or are not substantially, adversely affected by the envisaged addition(s).

In the ready-to-use composition with oxidizing agent, the oxidizing agent is preferably chosen from hydrogen peroxide, urea peroxide, alkali metal bromates or ferricyanides, and persalts such as perborates and persulfates. It is particularly preferred to use hydrogen peroxide. This oxidizing agent advantageously consists of an aqueous hydrogen peroxide solution whose titer may range, more particularly, from about 1 to 40 volumes and even more preferably from about 5 to 40 volumes.

Oxidizing agents that may also be used are one or more redox enzymes such as laccases, peroxidases and 2-electron oxidoreductases (such as uricase), where appropriate in the presence of their respective donor or cofactor.

The pH of the composition [composition with or without oxidizing agent] is generally between 2 and 12. It is preferably between 3 and 11 and more particularly between 7 and 10. It may be adjusted to the desired value using acidifying or basifying agents or buffers that are well known in the prior art in the dyeing of keratin fibers.

More preferably, when the composition contains an oxidizing agent for lightening fibers, the pH of the ready-to-use mixture is greater than 7 and even more preferably greater than 8.

Among the basifying agents that may be mentioned, for example, are aqueous ammonia, alkali metal carbonates, alkanolamines such as monoethanolamine, diethanolamine and triethanolamine and also derivatives thereof, oxyethylenated and/or oxypropylenated hydroxyalkylamines and ethylene-diamines, sodium hydroxide, potassium hydroxide and the compounds of formula (XIX) below:

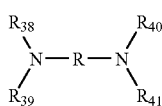

(XIX)

in which R is a propylene residue optionally substituted with a hydroxyl group or a $C_1$–$C_4$ alkyl radical; $R_{38}$, $R_{39}$, $R_{40}$ and $R_{41}$, which may be identical or different, represent a hydrogen atom, a $C_1$–$C_4$ alkyl radical or a $C_1$–$C_4$ hydroxyalkyl radical.

The acidifying agents are conventionally, for example, mineral or organic acids, for instance hydrochloric acid, orthophosphoric acid, carboxylic acids, for instance tartaric acid, citric acid or lactic acid, or sulfonic acids.

Among the buffers that may be mentioned are those sold by the company Merck under the brand name Titrisol, such as the phosphate buffer ($KH_2PO_4$ at 0.026 mol/l, $Na_2HPO_4$ at 0.041 mol/l) and the borate buffer ($H_3BO_3$ at 0.05 mol/l, KCl at 0.05 mol/l, NaOH at 0.022 mol/l).

The dyeing process according to the invention is performed at room temperature and consists in applying the dye composition according to the invention (prepared extemporaneously at the time of use) with or without oxidizing agent, onto wet or dry keratin fibers, and in leaving it to act for a leave-in time ranging from 5 seconds to 60 minutes approximately, more preferably from 10 seconds to 5 minutes approximately and more particularly from 30 seconds to 2 minutes approximately, rinsing the fibers and then optionally washing them with shampoo, followed by rinsing them again and drying them.

The process according to the invention has the advantage of requiring only very short application times, of about from 10 seconds to 5 minutes and more particularly from 30 seconds to 2 minutes.

It is possible to perform the process at higher temperatures, such as those produced by a hairstyling hood, about 40° C., or by blow-drying, about 70–80° C.

Concrete examples illustrating the invention are given below, without, however, having any limiting nature.

EXAMPLES 1 and 2

The direct dye compositions below were prepared:

| EXAMPLE | 1 | 2 |
|---|---|---|
| Nitro direct dye: 1-β-hydroxyethyloxy-3-methylamino-4-nitrobenzene | | 0.364 |
| (1-Methyl-1-phenyl)-2-(1-methine-4N-methylpyridinylium)hydrazine methyl sulfate | 0.364 | |
| Dicationic compound of formula (I) 1 | 0.423 | 0.212 |
| Hydroxyethylcellulose | 0.378 | 0.384 |
| Surfactant: (50/50 C8/C10)alkyl polyglucoside as an aqueous 60% solution | 2.95 | 3 |
| Polyethylene glycol (8EO) | 5.906 | 6 |
| Benzyl alcohol | 3.938 | 4 |
| Preserving agent: methyl, butyl, ethyl, propyl, and isobutyl p-hydroxybenzoate | 0.0032 | 0.0032 |
| pH 9 borate buffer | 49.99 | 50 |
| Demineralized water q.s. | 100 | 100 |

[amounts expressed as grams of Active Material (AM)]

Each of the compositions of examples 1 and 2 was applied to locks of natural gray hair containing 90% white hairs, for 20 minutes at room temperature (20° C.).

After the leave-in time, the locks of hair were rinsed and then dried. They were dyed in a matt [lacuna] shade with the composition of example 1 and a violet shade with the composition of example 2, and showed little selectivity and good resistance to washing.

EXAMPLE 3

The lightening direct dye composition below was prepared:

| EXAMPLE | 3 |
|---|---|
| Hydroxyethylcellulose | 1.39 |
| Aqueous ammonia (40% $NH_4OH$) | 2.08 |
| 40-volumes aqueous hydrogen peroxide solution | 60 |
| Dicationic compound of formula (I) 1 | 0.268 |
| (1-Methyl-1-phenyl)-2-(1-methine-4N-methylpyridinylium)hydrazine methyl sulfate | 0.230 |
| Demineralized water q.s. | 100 |

[amounts expressed as grams of Active Material (AM)]

The composition was applied to locks of natural gray hair containing 90% white hairs, for 35 minutes at room temperature (20° C.).

After the leave-in time, the locks of hair were rinsed and then dried. They were dyed in a matt yellow shade that showed little selectivity and good resistance to washing.

The invention claimed is:

1. A dye composition for human keratin fibers, comprising, in a medium that is suitable for dyeing, at least one direct dye, and at least one dicationic compound chosen from those of formulae (I), (II) and (III):

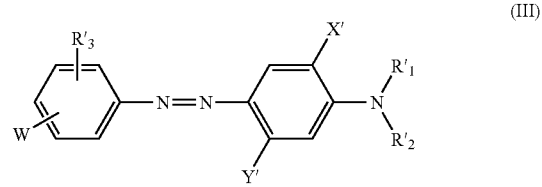

wherein:

A and A1, which may be identical or different, are chosen from radicals of formula (a)

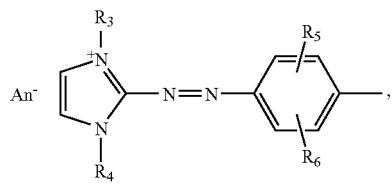

Z is chosen from aliphatic and aromatic radicals, $Z_1$ is an alkyl radical, $R_1$ and $R_2$, which may be identical or different, are chosen from hydrogen atoms, $(C_1-C_4)$alkyl radicals optionally substituted with at least one entity chosen from halogen atoms, hydroxyl, carboxyl and cyano radicals; $(C_1-C_4)$ alkoxy radicals optionally substituted with at least one radical chosen from hydroxyl and $(C_1-C_4)$alkoxy radicals; and amino, alkylamino, dialkylamino, aminocarbonyl, phenyl, phenoxy and phenylaminocarbonyl radicals, wherein the phenyl radicals are optionally substituted with at least one radical chosen from $(C_1-C_4)$alkyl, $(C_1-C_4)$alkoxy and phenoxy radicals, or $R_1$ and $R_2$ can form, together with the two nitrogen atoms that bear them and the radical Z, a piperazine ring, X is a bridging radical chosen from —CO—; —CO—CH$_2$—CH$_2$—CO—; —CO—CO—; 1,4-dicarbonylphenyl; —CH$_2$—CH$_2$—; and triazines of formulae (b) and (c):

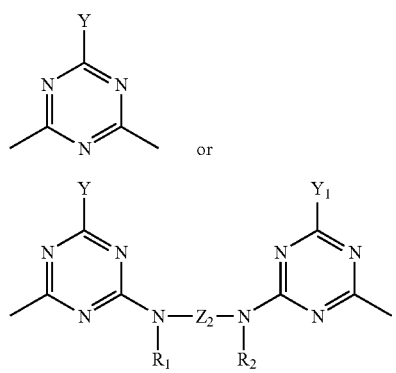

wherein:

Y and $Y_1$, which may be identical or different, are chosen from halogen atoms and hydroxyl, amino, monoalkylamino, dialkylamino, 1-piperidino, morpholino and 1-piperazino radicals, wherein the piperazino radicals are optionally substituted on the nitrogen atom not attached to the triazine ring with at least one $(C_1-C_4)$ alkyl radical, said alkyl radicals being optionally substituted with at least one radical chosen from hydroxyl, amino, mono$(C_1-C_4)$alkylamino and di$(C_1-C_4)$alkylamino radicals, $Z_2$ is chosen from $(C_2-C_8)$alkylene radicals, or alternatively, forms a piperazine ring with the two adjacent nitrogen atoms and the radicals $R_1$ and $R_2$, $R_3$ and $R_4$, which may be identical or different, are chosen from hydrogen atoms, $(C_1-C_4)$alkyl radicals optionally substituted with at least one entity chosen from halogen atoms, hydroxyl, carboxyl, and cyano radicals; $(C_1-C_4)$ alkoxy radicals optionally substituted with at least one radical chosen from hydroxyl and $(C_1-C_4)$alkoxy radicals; and amino, alkylamino, dialkylamino, aminocarbonyl, phenyl, phenoxy and phenylaminocarbonyl radicals, wherein the phenyl radicals are optionally substituted with at least one radical chosen from $(C_1-C_4)$alkyl, $(C_1-C_4)$alkoxy and phenoxy radicals, —$R_5$ and $R_6$, which may be identical or different, are chosen from hydrogen atoms; $(C_1-C_4)$alkoxy radicals optionally substituted with at least one radical chosen from hydroxyl, carboxyl, halogen and cyano radicals; $(C_1-C_4)$alkoxy radicals optionally substituted with at least one radical chosen from hydroxyl and $(C_1-C_4)$ alkoxy radicals; and amino, alkylamino, dialkylamino, aminocarbonyl, phenyl, phenoxy and phenylaminocarbonyl radicals, wherein the phenyl radicals are optionally substituted with at least one radical chosen from $(C_1-C_4)$alkyl, $(C_1-C_4)$alkoxy and phenoxy radicals, An$^-$ denotes an anion;

X' and Y', which may be identical or different, are chosen from hydrogen and halogen atoms, and $(C_1-C_4)$alkyl, $(C_1-C_4)$alkoxy, $(C_1-C_4)$alkylcarbonylamino, arylcarbonylamino, ureido and arylureido radicals, R'$_1$ is chosen from hydrogen atoms, optionally substituted alkyl and aryl radicals, and R'$_2$ radicals, R'$_2$ is a radical of formula (d):

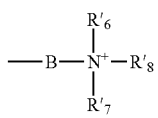

wherein:

B is chosen from linear and branched alkylene radicals,

R'$_6$ is chosen from hydrogen atoms and optionally substituted alkyl radicals,

R'$_7$ and R'$_8$, which may be identical or different, are chosen from optionally substituted alkyl radicals, R'$_6$ and R'$_7$, together with the nitrogen, form an optionally substituted 5-, 6- or 7-membered ring, which may comprise other hetero atoms, or alternatively R'$_6$, R'$_7$ and R'$_8$ together form a pyridinium ring, R'$_3$ is chosen from hydrogen and halogen atoms, and $(C_1-C_4)$alkyl $(C_1-C_4)$alkoxy radicals, W is a radical of formula (e):

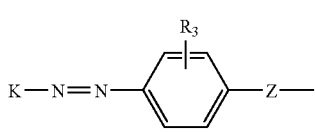

wherein:

K is a coupling radical,

Z is a bridging radical chosen from the radicals of formulae:

—NR'$_9$—CO—;   —CO—NR'$_9$—NR'$_9$—CO—;

—OC—N(piperazine)N—CO—

—OC—N(piperazine)N—B$_1$—NR'$_9$—CO—

—OC—NR$_9$—(cyclohexyl)—NR'$_9$—CO—

—OC—N'R$_9$—(phenyl with R'$_3$)—N'R$_9$—CO—

—OC—NR'$_9$—CH$_2$—(phenyl with R'$_3$)—CH$_2$—NR'$_9$—CO—

—OC—NR'$_9$—CH$_2$—(phenyl with R'$_3$)—NR'$_9$—CO— and —CO—NR'$_9$—B$_1$—NR'$_9$—CO—,
and wherein
R'$_9$ is chosen from hydrogen atoms and optionally substituted (C$_2$–C$_4$)alkyl radicals, and a
B$_1$ is chosen from linear and branched C$_2$–C$_{12}$ alkylene radicals optionally interrupted with at least one entity chosen from —NR'$_9$— radicals, and oxygen and sulfur atoms;
and wherein, in formula (III), the number of cationic charges is two.

2. The composition according to claim 1, wherein the human keratin fibers are hair.

3. The composition according to claim 1, wherein, in formula (I),
R$_1$ and R$_2$, which may be identical or different, are chosen from hydrogen atoms, (C$_1$–C$_4$)alkyl radicals substituted with hydroxyl radicals and (C$_1$–C$_4$)alkoxy radicals,
Z is chosen from linear, branched and cyclic C$_2$–C$_8$ alkyl radicals optionally substituted with at least one entity chosen from hydroxyl and alkoxy radicals and halogen atoms, the chain of said radical optionally being interrupted with an entity chosen from oxygen atoms and —NR$_1$— groups; and 1,4-phenyl radicals, 1,4-naphthyl radicals optionally substituted with at least one entity chosen from alkyl and alkoxy radicals and halogen atoms; Z possibly forming a piperazine ring together with R$_1$, R$_2$ and the two nitrogen atoms,
X is chosen from groups of formula (b).

4. The composition according to claim 3, wherein R$_1$ and R$_2$, which may be identical or different, are chosen from hydrogen atoms and methyl radicals.

5. The composition according to claim 3, wherein Z is chosen from unsubstituted phenyl radicals; phenyl and naphthyl radicals substituted with at least one entity chosen from methyl and methoxy radicals; piperazine radicals formed by bonding with R$_1$, R$_2$ and the two nitrogen atoms; and (C$_2$–C$_4$)alkylene radicals which are optionally substituted with at least one hydroxyl radical.

6. The composition according to claim 1, wherein, in formula (II):
Z$_1$ is chosen from linear, branched and cyclic C$_2$–C$_8$ alkyl radicals, optionally substituted with at least one entity chosen from hydroxyl and alkoxy radicals and halogen atoms, the chain of said radical optionally being interrupted with an entity chosen from oxygen atoms and —NR$_1$— groups; and a piperazine ring formed with R$_1$, R$_2$ and the two nitrogen atoms,
R$_3$ and R$_4$ are chosen from methyl and ethyl radicals, and
R$_5$ and R$_6$ are chosen from hydrogen atoms, and methyl and methoxy radicals.

7. The composition according to claim 6, wherein Z$_1$ is chosen from (C$_2$–C$_6$)alkylene radicals optionally substituted with at least one hydroxyl group; and a piperazine ring formed with R$_1$, R$_2$ and the two nitrogen atoms, 8. The composition according to claim 7, wherein Z$_1$ is chosen from unsubstituted (C$_2$–C$_4$)alkylene radicals.

9. The composition according to claim 1, wherein, in formula (III):
B of formula (d) is chosen from ethylene, n-propylene, isopropylene and n-butylene radicals,
K of formula (e) is a coupling compound chosen from those of formulae (f), (g) and (h):

(f) phenyl with X', Y' substituents and N(R'$_1$)(R'$_2$)

(g) H$_3$C—CO—CH$_2$—CO—NH—(phenyl with R'$_3$ and (K$_1$)$_n$)   or (h) H$_2$C(K$_1$)—CO—CH$_2$—CO—NH—(phenyl with R'$_3$)

wherein,
X', Y' and R'$_1$, R'$_2$, and R'$_3$ have the same meaning as in formula (III),
n is equal to 1 or 2, and
K$_1$ is a radical of formula:

—N$^+$(R'$_6$)(R'$_7$)—R'$_8$.

10. A dye composition for human keratin fibers, comprising, in a medium that is suitable for dyeing, at least one direct dye, provided that the direct dye is not chosen from Basic Blue 7, Basic Blue 26, Basic Blue 99, Basic Violet 10, Basic Violet 14, Basic Brown 16, Basic Brown 17, Basic Red 2, Basic Red 22, Basic Red 76, Basic Red 118, and Basic Yellow 57, and at least one dicationic compound of formula (IV):

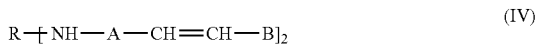

wherein, in formula (IV):
the groups [—NH-A-CH=CH—B] may be identical or different, and wherein
A is chosen from optionally substituted benzene rings,
B is chosen from radicals derived from heterocyclic compounds comprising a quaternized nitrogen comprising an entity chosen from active methyl and methylene radicals,
R is the residue of a crosslinking agent chosen from phosgene, halogenated triazines and halogenated pyrimidines.

11. The dye composition according to claim 10, wherein, in formula (IV),
B is chosen from quinolinium, picolinium, benzothiazolium, benzimidazolium, indolium and quinoxalinium derivatives;

A is chosen from benzene rings that are optionally substituted with at least one radical chosen from ($C_1$–$C_4$) alkoxy radicals, ($C_1$–$C_4$)alkyl radicals and halogen atoms; and R is halogenated triazine chosen from 2,4,6-trichlorotriazine, 2,4,6-trifluorotriazine, 2,4-dichloro-6-(dimethylaminopropylamino)triazine, 2,4-dichloro-6-hydroxytriazine, 2,4-difluoro-6-(trimethylaminoethylamino) triazine chloride, 2,4-difluoro-6-(N-carboxymethylamino)triazine, 2,4-dichloro-6-(N,N-dihydroxyethylamino)triazine, 2,4-difluoro-6-(N-hydroxypropylamino)triazine, 2,4-dichloro-6-(N,N-dimethylamino)triazine, 2,4-difluoro-6-(N,N-dihexylamino)triazine and 2,4-dichloro-6-(N-2-sulfoethylamino)triazine.

12. The dye composition according to claim 1, wherein the at least one compound of formula (I) is chosen from those of formulae (I)1 to (I)7:

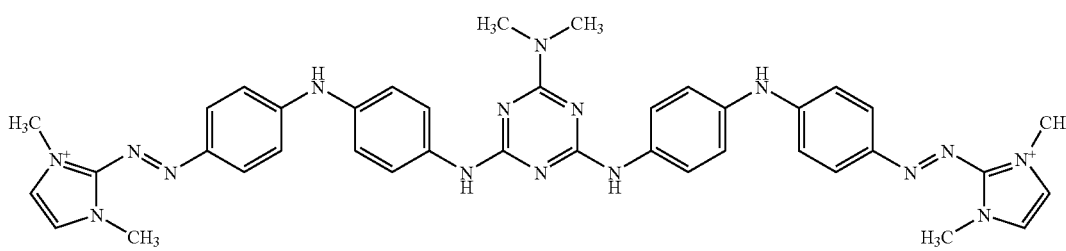

(I)1

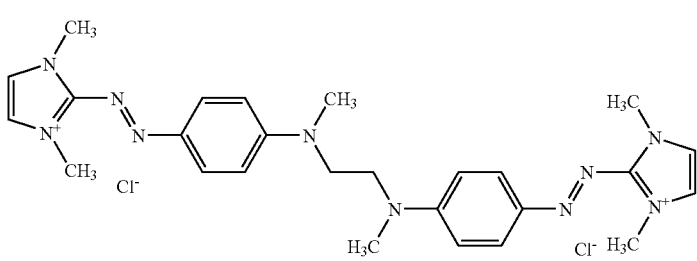

(I)2

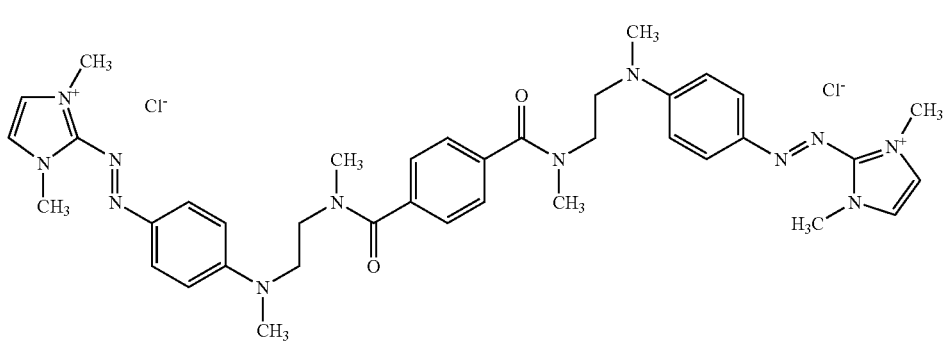

(I)3

-continued
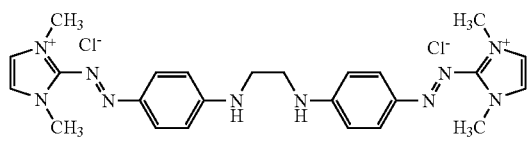 (I)4
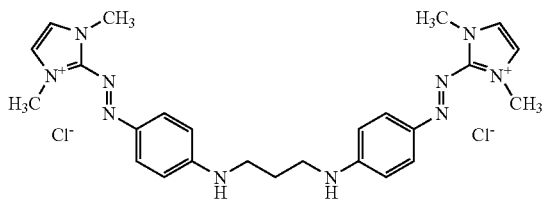 (I)5
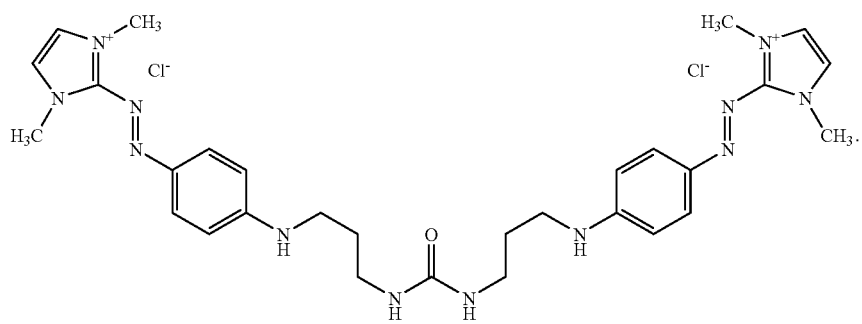 (I)6
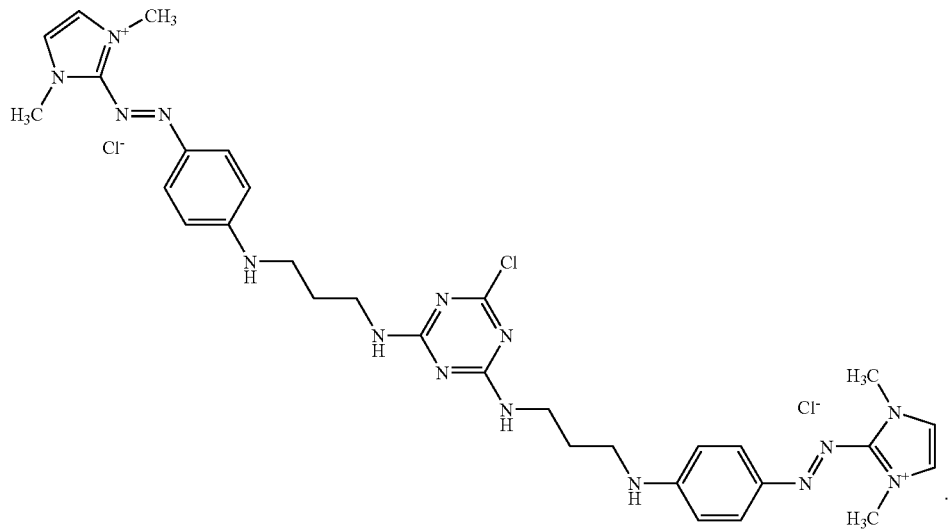 (I)7
13. The dye composition according to claim 1, wherein the at least one compound of formula (III) is the following compound:
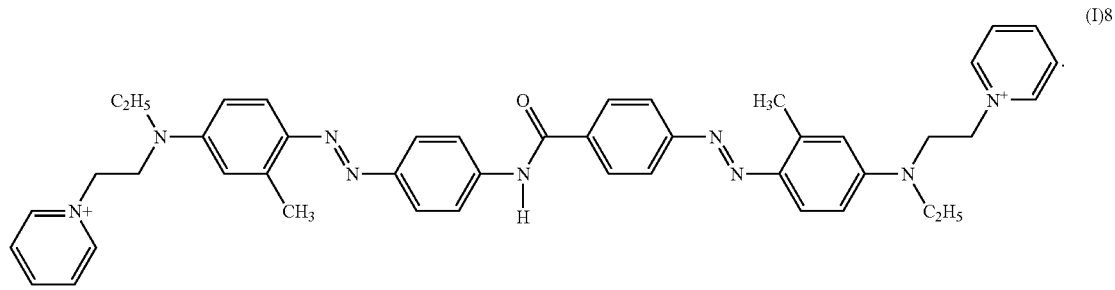 (I)8

14. The dye composition according to claim 10, wherein the at least one dicationic compound of formula (IV) is the following compound:

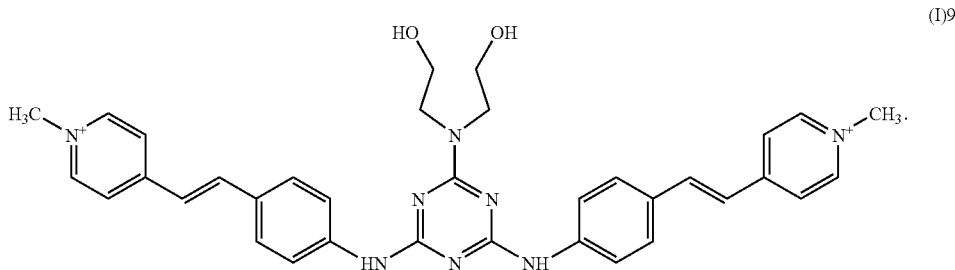

(I)9

15. The dye composition according to claim 1, wherein the at least one dicationic compound chosen from those of formulae (I), (II), and (III) is present in an amount ranging from 0.01 % to 40% by weight, relative to the total weight of the composition.

16. The dye composition according to claim 10, wherein the at least one dicationic compound of formula (IV) is present in an amount ranging from 0.01 % to 40% by weight, relative to the total weight of the composition.

17. The dye composition according to claim 1, wherein the at least one direct dye is chosen from neutral, acidic and cationic nitrobenzene direct dyes; neutral, acidic and cationic azo direct dyes; quinone direct dyes; azine direct dyes; triarylmethane direct dyes; indoamine direct dyes; cationic direct dyes comprising a quaternized nitrogen atom and a —CH=N— bond; and natural direct dyes.

18. The dye composition according to claim 17, wherein the at least one quinone direct dye is chosen from neutral, acidic and cationic anthraquinones.

19. The dye composition according to claim 1, wherein the at least one direct dye is present in an amount ranging from 0.001% to 20% by weight, relative to the total weight of the composition.

20. The dye composition according to claim 1, further comprising, in an amount ranging from 0.01% to 10% by weight, relative to the total weight of the composition, at least one cationic or amphoteric polymer chosen from:

dimethyldiallylammonium chloride homopolymers;

polymers comprising repeating units of formula (W) and (U):

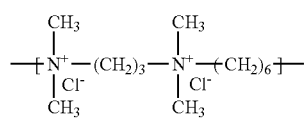
(W)

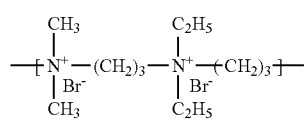
(U)

polymers comprising units of formula (IX):

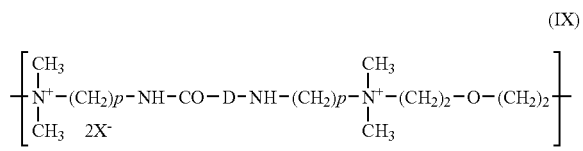
(IX)

wherein p is equal to 3,

D is chosen from a bond, —(CH$_2$)$_4$—CO— groups, —(CH$_2$)$_7$—CO— group groups, and X is a chlorine atom, or, alternatively, D may be chosen from block copolymers formed from units corresponding to the polymers when D is chosen from a bond and —(CH$_2$)$_4$—CO— groups; and copolymers of acrylic acid and of dimethyldiallylammonium chloride.

21. The dye composition according to claim 10, further comprising, in an amount ranging from 0.01% to 10% by weight, relative to the total weight of the composition, at least one cationic or amphoteric polymer chosen from:

dimethyldiallylammonium chloride homopolymers;

polymers comprising repeating units of formula (W) and (U):

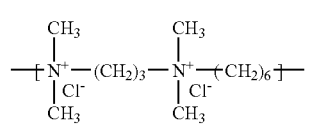
(W)

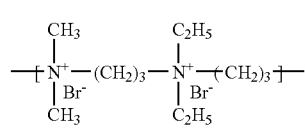
(U)

polymers comprising units of formula (IX):

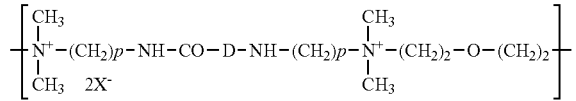
(IX)

wherein p is equal to 3,

D is chosen from a bond, —(CH$_2$)$_4$—CO— groups, —(CH$_2$)$_7$—CO— group groups, and X is a chlorine atom, or, alternatively, D may be chosen from block copolymers formed from units corresponding to the polymers when D is chosen from a bond and —(CH$_2$)$_4$—CO— groups; and copolymers of acrylic acid and of dimethyidiallylammonium chloride.

22. The dye composition according to claim 1, further comprising at least one surfactant chosen from anionic, cationic, nonionic and amphoteric surfactants.

23. The dye composition according to claim 10, further comprising at least one surfactant chosen from anionic, cationic, nonionic and amphoteric surfactants.

24. A process for dyeing human keratin fibers, comprising applying to the keratin fibers, which may be dry or wet, a dye composition comprising, in a medium that is suitable for dyeing, at least one direct dye, and at least one dicationic compound chosen from those of formulae (I), (II) and (III):

$$[A-\underset{R_1}{N}-Z-\underset{R_2}{N}]_p-X \quad (I)$$

$$A-\underset{R_1}{N}-Z_1-\underset{R_2}{N}-A_1 \quad (II)$$

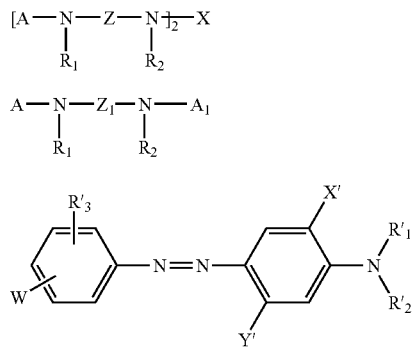
(III)

wherein:

A and A1, which may be identical or different, are chosen from radicals of formula (a)

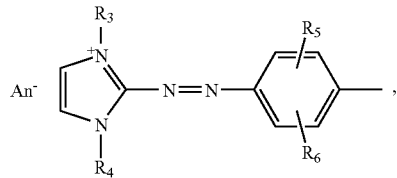
(a)

Z is chosen from aliphatic and aromatic radicals,

Z$_1$ is an alkyl radical,

R$_1$ and R$_2$, which may be identical or different, are chosen from hydrogen atoms, (C$_1$–C$_4$)alkyl radicals optionally substituted with at least one entity chosen from halogen atoms, hydroxyl, carboxyl and cyano radicals; (C$_1$–C$_4$) alkoxy radicals optionally substituted with at least one radical chosen from hydroxyl and (C$_1$–C$_4$)alkoxy radicals; and amino, alkylamino, dialkylamino, aminocarbonyl, phenyl, phenoxy and phenylaminocarbonyl radicals, wherein the phenyl radicals are optionally substituted with at least one radical chosen from (C$_1$–C$_4$)alkyl, (C$_1$–C$_4$)alkoxy and phenoxy radicals, or R$_1$ and R$_2$ can form, together with the two nitrogen atoms that bear them and the radical Z, a piperazine ring, X is a bridging radical chosen from —CO—; —CO—CH$_2$—CH$_2$—CO—; —CO—CO—; 1,4-dicarbonylphenyl; —CH$_2$—CH$_2$—; and triazines of formulae (b) and (c):

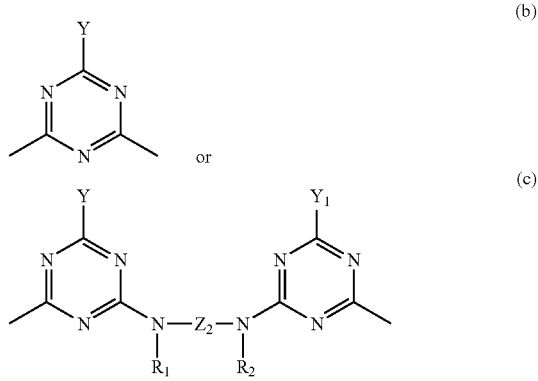

wherein:

Y and Y$_1$, which may be identical or different, are chosen from halogen atoms and hydroxyl, amino, monoalkylamino, dialkylamino, 1-piperidino, morpholino and 1-piperazino radicals, wherein the piperazino radicals are optionally substituted on the nitrogen atom not attached to the triazine ring with at least one (C$_1$–C$_4$) alkyl radical, said alkyl radicals being optionally substituted with at least one radical chosen from hydroxyl, amino, mono(C$_1$–C$_4$)alkylamino and di(C$_1$–C$_4$)alkylamino radicals, Z$_2$ is chosen from (C$_2$–C$_8$)alkylene radicals, or alternatively, forms a piperazine ring with the two adjacent nitrogen atoms and the radicals R$_1$ and R$_2$, R$_3$ and R$_4$, which may be identical or different, are chosen from hydrogen atoms, (C$_1$–C$_4$)alkyl radicals optionally substituted with at least one entity chosen from halogen atoms, hydroxyl, carboxyl, and cyano radicals; (C$_1$–C$_4$) alkoxy radicals optionally substituted with at least one radical chosen from hydroxyl and (C$_1$–C$_4$)alkoxy radicals; and amino, alkylamino, dialkylamino, aminocarbonyl, phenyl, phenoxy and phenylaminocarbonyl radicals, wherein the phenyl radicals are optionally substituted with at least one radical chosen from (C$_1$–C$_4$)alkyl, (C$_1$–C$_4$)alkoxy and phenoxy radicals, R$_5$ and R$_6$, which may be identical or different, are chosen from hydrogen atoms; (C$_1$–C$_4$)alkoxy radicals optionally substituted with an entity chosen from hydroxyl, carboxyl, halogen and cyano radicals; (C$_1$–C$_4$)alkoxy radicals optionally substituted with at least one radical chosen from hydroxyl and (C$_1$–C$_4$)alkoxy radicals; and amino, alkylamino, dialkylamino, aminocarbonyl, phenyl, phenoxy and phenylaminocarbonyl radicals, wherein the phenyl radicals are optionally substituted with at least one radical chosen from (C$_1$–C$_4$)alkyl, (C$_1$–C$_4$)alkoxy and phenoxy radicals, An$^-$ denotes an anion;

X' and Y', which may be identical or different, are chosen from hydrogen and halogen atoms, and (C$_1$–C$_4$)alkyl, (C$_1$–C$_4$)alkoxy, (C$_1$–C$_4$)alkylcarbonylamino, arylcarbonylamino, ureido and arylureido radicals, R'$_1$ is chosen from hydrogen atoms, optionally substituted alkyl and aryl radicals, and R'$_2$ radicals, R'$_2$ is a radical of formula (d):

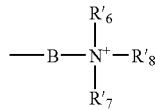 (d)

wherein:

B is chosen from linear and branched alkylene radicals,

R'$_6$ is chosen from hydrogen atoms and optionally substituted alkyl radicals,

R'$_7$ and R'$_8$, which may be identical or different, are chosen from optionally substituted alkyl radicals, R'$_6$ and R'$_7$, together with the nitrogen, form an optionally substituted 5-, 6- or 7-membered ring, which may comprise other hetero atoms, or alternatively R'$_6$, R'$_7$ and R'$_8$ together form a pyridinium ring, R'$_3$ is chosen from hydrogen and halogen atoms, and (C$_1$–C$_4$)alkyl (C$_1$–C$_4$)alkoxy radicals, W is a radical of formula (e):

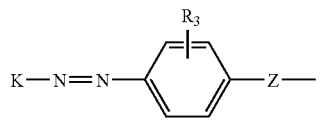 (e)

wherein:

K is a coupling radical,

Z is a bridging radical chosen from the radicals of formulae:

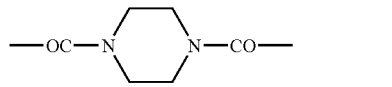

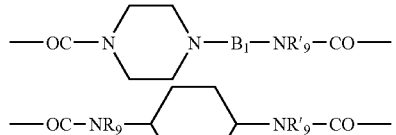

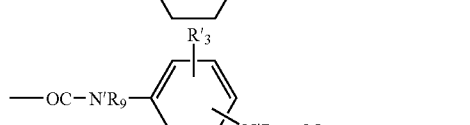

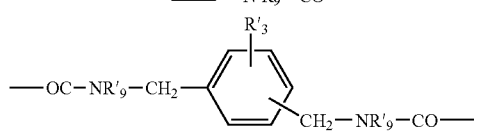

and —CO—NR'$_9$—B$_1$—NR'$_9$—CO—, and wherein

R'$_9$ is chosen from hydrogen atoms and optionally substituted (C$_2$–C$_4$)alkyl radicals, and B$_1$ is chosen from linear and branched C$_2$–C$_{12}$ alkylene radicals optionally interrupted with at least one entity chosen from —NR'$_9$— radicals, and oxygen and sulfur atoms;

and wherein, in formula (III), the number of cationic charges is two;

leaving the dye composition to act on the keratin fibers for a leave-in time ranging from 5 seconds to 60 minutes;

rinsing the keratin fibers and optionally washing the keratin fibers with shampoo, followed by rinsing them again and drying them.

25. A process for dyeing human keratin fibers comprising applying to the keratin fibers, which may be dry or wet, a composition comprising, in a medium that is suitable for dyeing, at least one direct dye, provided that the at least one direct dye is not chosen from the basic dyes, and at least one dicationic compound of formula (IV):

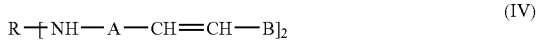 (IV)

wherein, in formula (IV):

the groups [—NH-A-CH=CH—B] may be identical or different, and wherein

A is chosen from optionally substituted benzene rings,

B is chosen from radicals derived from heterocyclic compounds comprising a quaternized nitrogen comprising an entity chosen from active methyl and methylene radicals, R is the residue of a crosslinking agent chosen from phosgene, halogenated triazines and halogenated pyrimidines;

leaving the dye composition to act on the keratin fibers for a leave-in time ranging from 5 seconds to 60 minutes;

rinsing the keratin fibers and optionally washing the keratin fibers with shampoo, followed by rinsing them again and drying them.

26. The process according to claim 24, wherein the dye composition further comprises at least one oxidizing agent.

27. The process according to claim 26, wherein the at least one oxidizing agent is mixed with the dye composition just before application to the keratin fibers.

28. The process according to claim 25, wherein the dye composition further comprises at least one oxidizing agent.

29. The process according to claim 28, wherein the at least one oxidizing agent is mixed with the dye composition just before application to the keratin fibers.

30. A multi-compartment kit for the direct lightening dyeing of human keratin fibers, comprising at least one first compartment comprising, in a medium that is suitable for dyeing, at least one direct dye, and at least one dicationic compound chosen from those of formulae (I), (II) and (III):

 (I)

-continued

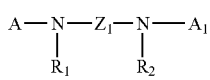
(II)

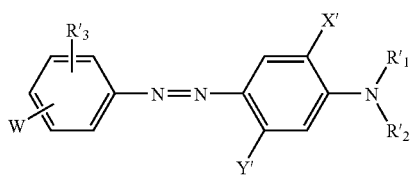
(III)

wherein:
A and A1, which may be identical or different, are chosen from radicals of formula (a)

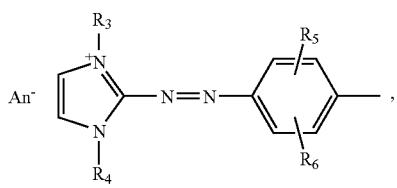
(a)

Z is chosen from aliphatic and aromatic radicals,
$Z_1$ is an alkyl radical,
$R_1$ and $R_2$, which may be identical or different, are chosen from hydrogen atoms, $(C_1-C_4)$alkyl radicals optionally substituted with at least one entity chosen from halogen atoms, hydroxyl, carboxyl and cyano radicals; $(C_1-C_4)$alkoxy radicals optionally substituted with at least one radical chosen from hydroxyl and $(C_1-C_4)$alkoxy radicals; and amino, alkylamino, dialkylamino, aminocarbonyl, phenyl, phenoxy and phenylaminocarbonyl radicals, wherein the phenyl radicals are optionally substituted with at least one radical chosen from $(C_1-C_4)$alkyl, $(C_1-C_4)$alkoxy and phenoxy radicals, or $R_1$ and $R_2$ can form, together with the two nitrogen atoms that bear them and the radical Z, a piperazine ring,
X is a bridging radical chosen from —CO—; —CO—$CH_2$—$CH_2$—CO—; —CO—CO—; 1,4-dicarbonylphenyl; —$CH_2$—$CH_2$—; and triazines of formulae (b) and (c):

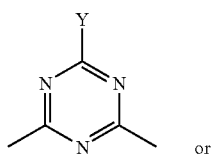
(b)

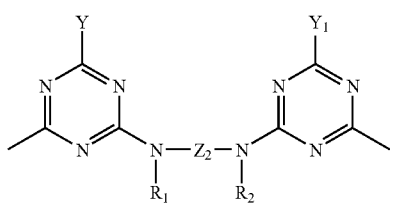
(c)

wherein:

Y and $Y_1$, which may be identical or different, are chosen from halogen atoms and hydroxyl, amino, monoalkylamino, dialkylamino, 1-piperidino, morpholino and 1-piperazino radicals, wherein the piperazino radicals are optionally substituted on the nitrogen atom not attached to the triazine ring with at least one $(C_1-C_4)$ alkyl radical, said alkyl radicals being optionally substituted with at least one radical chosen from hydroxyl, amino, mono$(C_1-C_4)$alkylamino and di$(C_1-C_4)$alkylamino radicals, $Z_2$ is chosen from $(C_2-C_8)$alkylene radicals, or alternatively, forms a piperazine ring with the two adjacent nitrogen atoms and the radicals $R_1$ and $R_2$, $R_3$ and $R_4$, which may be identical or different, are chosen from hydrogen atoms, $(C_1-C_4)$alkyl radicals optionally substituted with at least one entity chosen from halogen atoms, hydroxyl, carboxyl, and cyano radicals; $(C_1-C_4)$ alkoxy radicals optionally substituted with at least one radical chosen from hydroxyl and $(C_1-C_4)$alkoxy radicals; and amino, alkylamino, dialkylamino, aminocarbonyl, phenyl, phenoxy and phenylaminocarbonyl radicals, wherein the phenyl radicals are optionally substituted with at least one radical chosen from $(C_1-C_4)$alkyl, $(C_1-C_4)$alkoxy and phenoxy radicals, $R_5$ and $R_6$, which may be identical or different, are chosen from hydrogen atoms; $(C_1-C_4)$alkyl radicals optionally substituted with an entity chosen from hydroxyl, carboxyl, halogen and cyano radicals; $(C_1-C_4)$alkoxy radicals optionally substituted with at least one radical chosen from hydroxyl and $(C_1-C_4)$alkoxy radicals; and amino, alkylamino, dialkylamino, aminocarbonyl, phenyl, phenoxy and phenylaminocarbonyl radicals, wherein the phenyl radicals are optionally substituted with at least one radical chosen from $(C_1-C_4)$alkyl, $(C_1-C_4)$alkoxy and phenoxy radicals, An⁻ denotes an anion;

X' and Y', which may be identical or different, are chosen from hydrogen and halogen atoms, and $(C_1-C_4)$alkyl, $(C_1-C_4)$alkoxy, $(C_1-C_4)$alkylcarbonylamino, arylcarbonylamino, ureido and arylureido radicals, $R'_1$ is chosen from hydrogen atoms, optionally substituted alkyl and aryl radicals, and $R'_2$ radicals, $R'_2$ is a radical of formula (d):

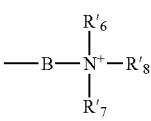
(d)

wherein:

B is chosen from linear and branched alkylene radicals, $R'_6$ is chosen from hydrogen atoms and optionally substituted alkyl radicals, $R'_7$ and $R'_8$, which may be identical or different, are chosen from optionally substituted alkyl radicals, $R'_6$ and $R'_7$, together with the nitrogen, form an optionally substituted 5-, 6- or 7-membered ring, which may comprise other hetero atoms, or alternatively $R'_6$, $R'_7$ and $R'_8$ together form a pyridinium ring, $R'_3$ is chosen from hydrogen and halogen atoms, and $(C_1-C_4)$alkyl $(C_1-C_4)$alkoxy radicals, W is a radical of formula (e):

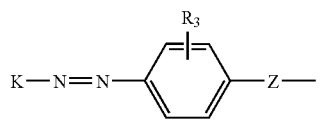

wherein:
K is a coupling radical,
Z is a bridging radical chosen from the radicals of formulae:

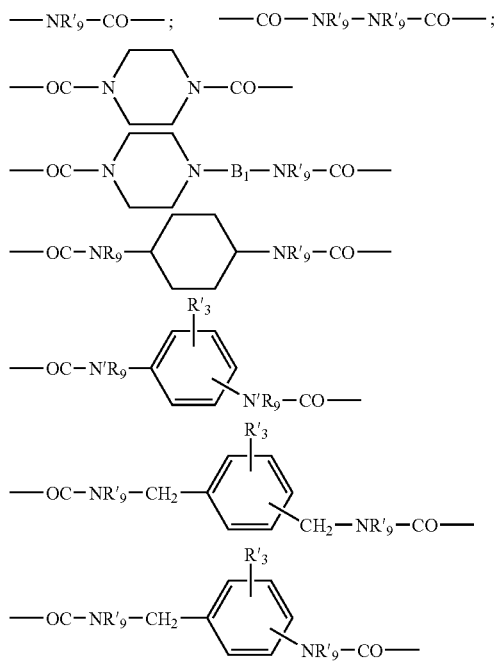

and —CO—NR'$_9$—B$_1$—NR'$_9$—CO—,
and wherein
R'$_9$ is chosen from hydrogen atoms and optionally substituted (C$_2$–C$_4$)alkyl radicals, and
B$_1$ is chosen from linear and branched C$_2$–C$_{12}$ alkylene radicals optionally interrupted with at least one entity chosen from —NR'$_9$— radicals, and oxygen and sulfur atoms;
and wherein, in formula (III), the number of cationic charges is two; and
at least one second compartment comprising at least one oxidizing agent.

31. A multi-compartment kit for the direct lightening dyeing of human keratin fibers, comprising
at least one first compartment comprising, in a medium suitable for dyeing, at least one direct dye, provided that the at least one direct dye is not chosen from the basic dyes, and
at least one dicationic compound of formula (IV):

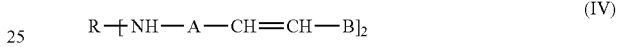

wherein, in formula (IV):
the groups [—NH-A-CH=CH—B] may be identical or different, and wherein
A is chosen from optionally substituted benzene rings,
B is chosen from radicals derived from heterocyclic compounds comprising a quaternized nitrogen comprising an entity chosen from active methyl and methylene radicals,
R is the residue of a crosslinking agent chosen from phosgene, halogenated triazines and halogenated pyrimidine; and
at least one second compartment comprising at least one oxidizing agent.

* * * * *

UNITED STATES PATENT AND TRADEMARK OFFICE
CERTIFICATE OF CORRECTION

| | | |
|---|---|---|
| PATENT NO. | : 7,189,266 B2 | Page 1 of 1 |
| APPLICATION NO. | : 10/480168 | |
| DATED | : March 13, 2007 | |
| INVENTOR(S) | : Grégory Plos et al. | |

It is certified that error appears in the above-identified patent and that said Letters Patent is hereby corrected as shown below:

On the title page, item (57), line 4, "on" should read --one--.

On the title page, item (57), line 6, "as a the" should read --as the--.

In claim 1, column 38, line 13, "—$R_5$" should read --$R_5$--.

In claim 7, column 40, line 19, "atoms," should read --atoms.--.

In claim 13, column 43, line 51, "(Ill)" should read --(III)--.

In claim 15, column 45, line 21, "(Ill)" should read --(III)--.

In claim 20, column 46, line 30, "-$(CH_2)_7$-CO- group groups," should read -- -$(CH_2)_7$-CO- groups,--.

In claim 21, column 47, line 4, "-$(CH_2)_7$-CO- group groups," should read -- -$(CH_2)_7$-CO-groups,--.

In claim 21, column 47, lines 9-10, "dimethyidiallylammonium" should read --dimethyldiallylammonium--.

Signed and Sealed this

Twenty-ninth Day of May, 2007

JON W. DUDAS
*Director of the United States Patent and Trademark Office*